(12) United States Patent
Engeberg et al.

(10) Patent No.: US 10,092,349 B2
(45) Date of Patent: Oct. 9, 2018

(54) VARIABLE-FREQUENCY STIMULATOR FOR ELECTROSURGERY

(75) Inventors: Erik Engeberg, Cuyahoga Falls, OH (US); Eric Espinal, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 499 days.

(21) Appl. No.: 14/115,481

(22) PCT Filed: May 4, 2012

(86) PCT No.: PCT/US2012/036532
§ 371 (c)(1),
(2), (4) Date: Nov. 4, 2013

(87) PCT Pub. No.: WO2012/151493
PCT Pub. Date: Nov. 8, 2012

(65) Prior Publication Data
US 2014/0074084 A1  Mar. 13, 2014

Related U.S. Application Data

(60) Provisional application No. 61/482,462, filed on May 4, 2011.

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1206* (2013.01); *A61B 18/14* (2013.01);
(Continued)

(58) Field of Classification Search
CPC .......... A61B 2018/00755; A61B 2018/00845; A61B 18/10; A61B 18/1206
See application file for complete search history.

(56) References Cited

U.S. PATENT DOCUMENTS 4,566,454 A * 1/1986 Mehl ...................... A61B 18/14
606/36
5,458,598 A * 10/1995 Feinberg ............ A61B 18/1445
606/205

(Continued)

*Primary Examiner* — Ronald Hupczey, Jr.
*Assistant Examiner* — Bo Ouyang
(74) *Attorney, Agent, or Firm* — Renner, Kenner, Greive, Bobak, Taylor & Weber Co. LPA

(57) ABSTRACT

A variable-frequency stimulator for electrosurgery includes an impedance analyzer to identify the electrical impedance of biological tissue being treated by an electrosurgical instrument, such as a laparoscope. Based on the identified tissue impedance, a controller adjusts the frequency of electrical current delivered to the electrosurgical instrument to reduce, minimize or normalize the impedance of the tissue, thereby preventing collateral damage to the tissue in and about the surgical site. Additionally, the laparoscope may be configured with multiple electrically conductive grasping arms that are used to deliver the electrical current to the surgical site. The conductive grasping arms provide multiple current paths for the electrical current to flow, thus concentrating the electrical current at the surgical site during an electrosurgical procedure. Thus, the unwanted spread of electrical current in the tissue is prevented, resulting in the reduction or prevention of collateral damage to tissue in and about the surgical site.

9 Claims, 41 Drawing Sheets

(52) U.S. Cl.
CPC .............. *A61B 2018/00428* (2013.01); *A61B 2018/00595* (2013.01); *A61B 2018/00607* (2013.01); *A61B 2018/00642* (2013.01); *A61B 2018/00702* (2013.01); *A61B 2018/00726* (2013.01); *A61B 2018/00732* (2013.01); *A61B 2018/00797* (2013.01); *A61B 2018/00875* (2013.01); *A61B 2018/128* (2013.01); *A61B 2018/1455* (2013.01); *A61B 2018/1457* (2013.01)

(56) References Cited

U.S. PATENT DOCUMENTS

| | | | |
|---|---|---|---|
| 8,958,887 B2* | 2/2015 | Hancock | A61B 10/0233 600/562 |
| 2003/0130711 A1* | 7/2003 | Pearson | A61B 18/1477 607/101 |
| 2005/0177150 A1* | 8/2005 | Amoah | A61B 18/1206 606/34 |
| 2009/0143789 A1* | 6/2009 | Houser | A61B 17/0057 606/142 |
| 2010/0179536 A1* | 7/2010 | Podhajsky | A61B 18/1206 606/34 |
| 2012/0239026 A1* | 9/2012 | Orszulak | A61B 18/1206 606/35 |

* cited by examiner

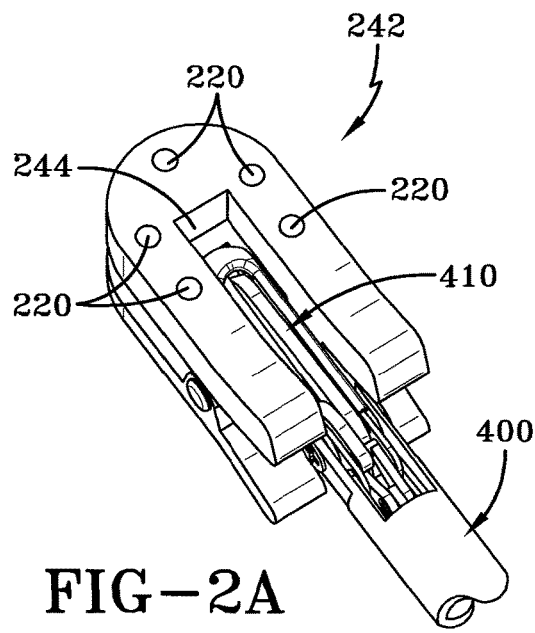
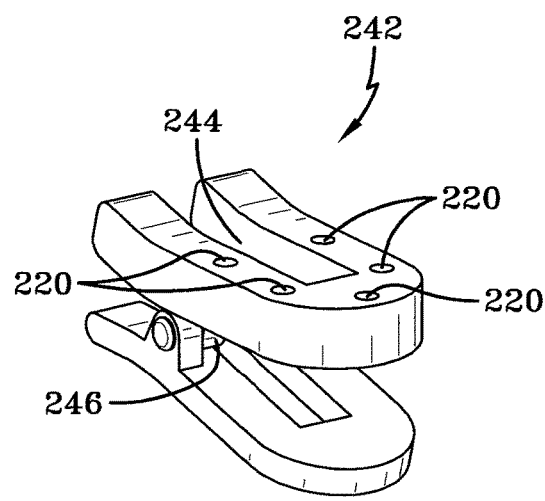
FIG-2A    FIG-2B
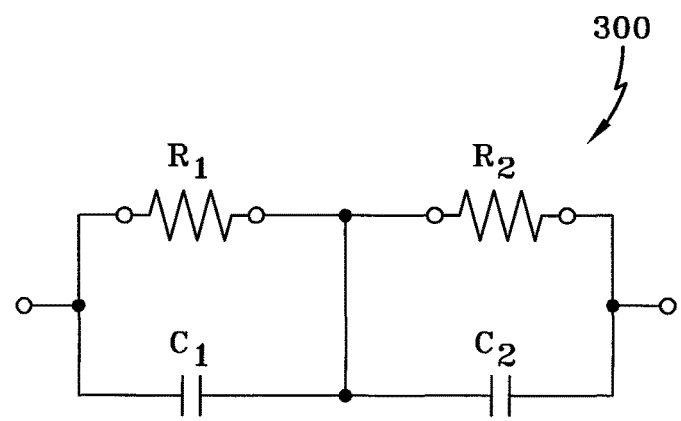
FIG-3

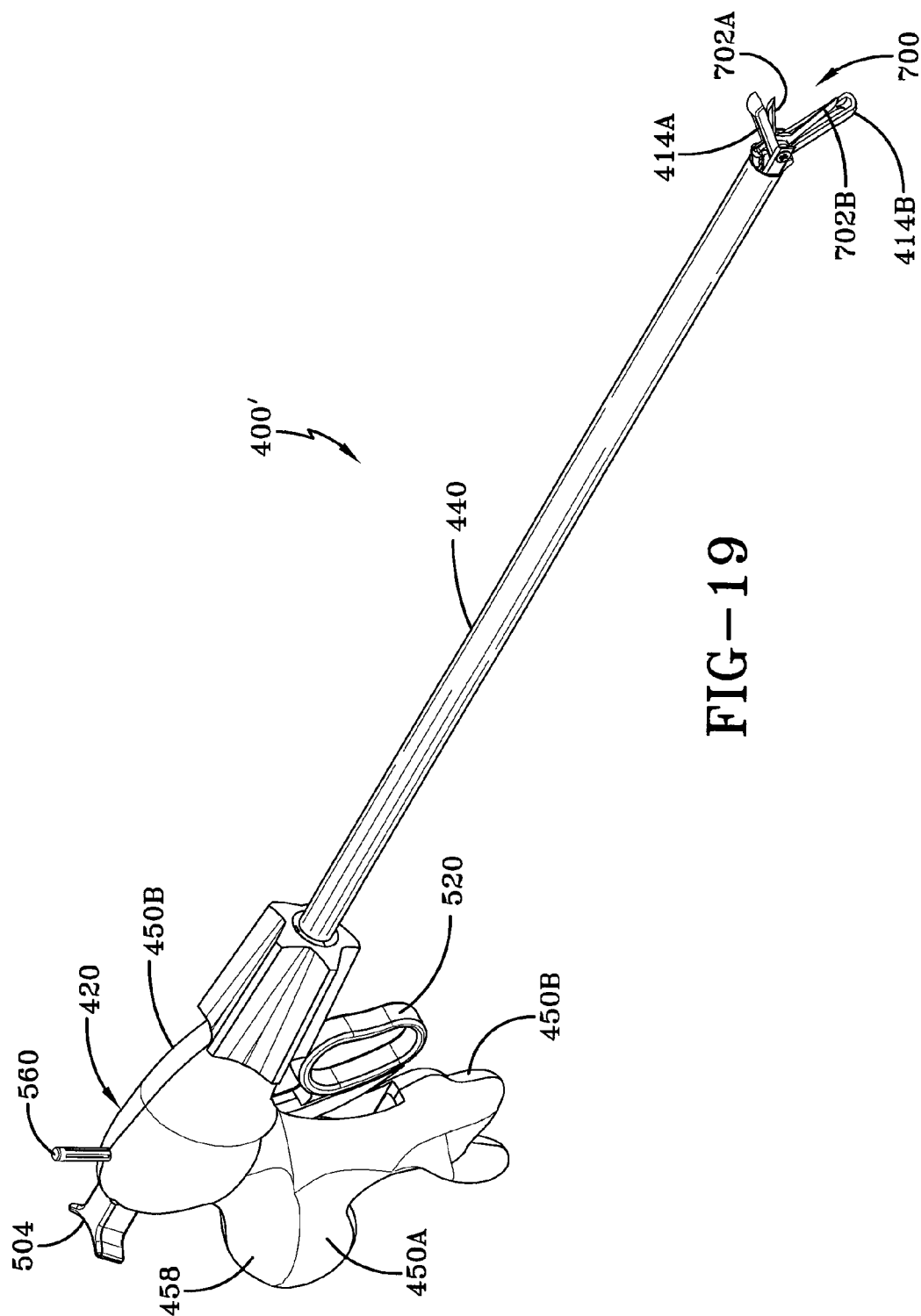

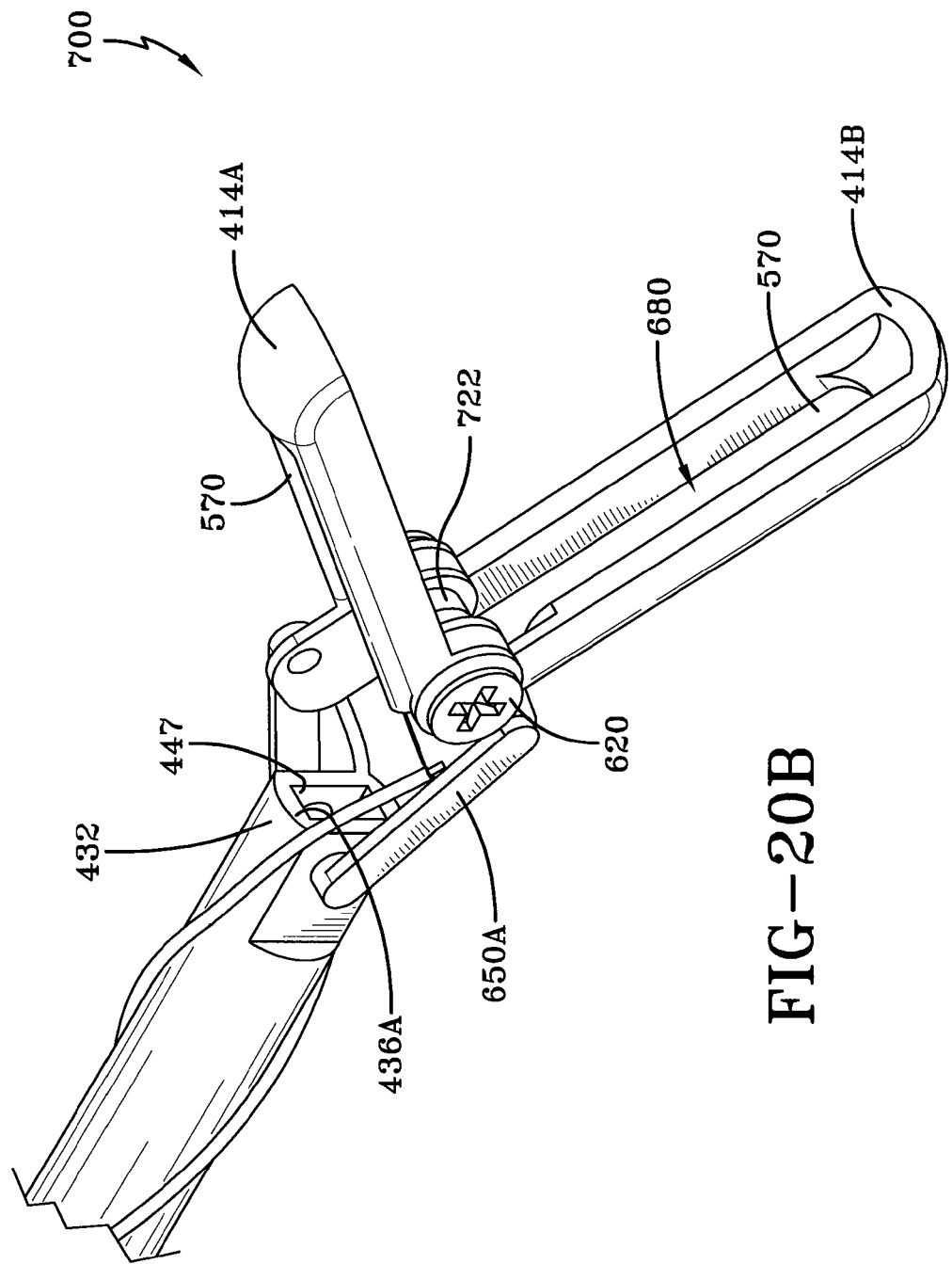

VARIABLE-FREQUENCY STIMULATOR FOR ELECTROSURGERY

TECHNICAL FIELD

Generally, the present invention relates to surgical devices used to perform electrosurgery. In particular, the present invention relates to a variable-frequency stimulator used to perform electrosurgery that optimizes the frequency of applied electrical current to reduce the electrical impedance of the biological tissue being treated. More particularly, the present invention relates to a variable-frequency stimulator and laparoscope configured to deliver electrical current to biological tissue at multiple contact points to minimize the spread of electrical current through the tissue, so as to prevent collateral damage to tissue surrounding the surgical site.

BACKGROUND ART

Electrosurgery is a widely accepted technique and is used to perform a variety of manual or robot-assisted surgical procedures on biological tissue. For example, electrosurgery is used to hemostatically occlude blood vessels, as well as to perform tonsillectomies, vaginal hysterectomies, and amputation of the liver tip and splenic wedge, as well as to treat polycystic ovary syndrome, remove benign and malignant lesions of the skin, and to perform intradiscal electrothermal therapy for internal disc disruptions of the spine. However, surgeons that utilize currently available robotic and manual laparoscopic electrostimulation devices for electrosurgery are often unable to prevent collateral damage, such as the overheating, charring, and tearing of the tissue surrounding the surgical site. Collateral damage is caused by the uncontrolled spread of energy from the electrostimulation device through tissue that is located in and about the surgical site. Furthermore, the rate of collateral damage caused by laparoscopic electrosurgical stimulators due to the uncontrolled spread of electricity also tends to increase with repeated use of such electrosurgical devices. Unfortunately, such collateral damage often leads to surgical complications, increased pain and discomfort, and longer hospital stays, which increase the costs to the patient.

Although current commercially-available electrosurgical devices use a constant stimulation frequency that is between about 300 kHz to 3 MHz, for example, the biological tissue being treated by such devices has a conductivity that is dependent on the stimulation frequency used. For example, biological tissue, including kidney, liver, lung, heart, spleen, uterus, thyroid, testes, ovary, bladder, tongue, cartilage, muscle, and skin tissue all have an electrical conductivity that tends to increase with increasing stimulation frequencies. However, there are many other examples showing that the conductivity of these tissues can increase by more than two orders of magnitude over a frequency range from 10 Hz to 20 GHz. In addition, changes in electrical conductivity in biological tissue may also be caused by mechanical changes in the structure of biological tissue itself. For example, it has been shown that the electrical conductivity of porcine lung tissue has a large variation in depending on whether the lung is inflated or deflated, which is due to the significant mechanical changes of the structure of the lung during pneumoconstriction. Thus, a wide array of electrosurgical procedures can be positively impacted by providing a variable-frequency stimulator device that is able to deliver an adjustable stimulation frequency to increase the conductivity of the tissue being treated.

In addition, while electrosurgical techniques have improved due to various technological breakthroughs, including advancements in controlling the electrical current, clinically-relevant problems still exist with robotic and manual laparoscopic electrosurgical devices. Thus, surgeons still have difficulty avoiding collateral damage in and about the surgical site being treated by electrosurgical devices. As such, surgical complications from electrosurgery still frequently occur, which result in patient dissatisfaction and increased hospitalization costs, which are unwanted.

Therefore, there is a need for a variable-frequency stimulator for electrosurgery, which controls the conductivity of the biological tissue by varying a stimulation frequency. In addition, there is a need for a variable-frequency stimulator for electrosurgery that can be readily used with any commercially available robotic or manual electrosurgical device, such as a tissue dissector or laparoscope. There is also a need for a variable-frequency stimulator that provides improved electrosurgical efficacy and safety margins, and that reduces the occurrence of collateral damage to tissue surrounding the surgical site being treated. Moreover, there is a need for a laparoscope for use with a variable-frequency stimulator that is configured to concentrate the electrical current near the surface of the surgical site to prevent the uncontrolled spread of electrical current through the tissue, so as to reduce or prevent collateral damage to nearby tissue.

SUMMARY OF INVENTION

In light of the foregoing, it is a first aspect of the present invention to provide a variable-frequency stimulator for performing electrosurgery on tissue comprising a controller; a switch coupled to said controller, said switch configured to be placed into either of a first state or a second state; a surgical instrument coupled to said switch, said surgical instrument configured to contact the tissue; an impedance analyzer coupled to said controller and to said switch, said impedance analyzer configured to identify the impedance of tissue over a range of frequencies; and a frequency generator coupled to said controller and to said switch, said frequency generator configured to generate an electrical signal at a frequency greater than about 3 MHz, wherein when said switch is in said first state and said surgical instrument is in contact with the tissue, said impedance analyzer is electrically coupled to said surgical instrument to identify a frequency or range of frequencies in said frequency range that lowers the impedance and/or increases the conductivity of the tissue, and when said switch is in said second state, said frequency generator is coupled to said surgical instrument, so as to apply said electrical signal at said identified frequency or range of frequencies to the tissue.

It is another aspect of the present invention to provide a variable-frequency stimulator for performing electrosurgery on tissue comprising a controller; a switch coupled to said controller, said switch configured to be placed into either of a first state or a second state; a surgical instrument coupled to said switch, said surgical instrument configured to contact the tissue; an impedance analyzer coupled to said controller and to said switch, said impedance analyzer configured to identify the impedance of tissue over a range of frequencies; and a frequency generator coupled to said controller and to said switch, said frequency generator configured to generate an electrical signal; and wherein when said switch is in said first state and said surgical instrument is in contact with the tissue, said impedance analyzer is electrically coupled to said surgical instrument to identify the lowest impedance of the tissue that is associated with said frequency range, said impedance analyzer also identifying a test impedance in the tissue at a predetermined test frequency, said controller calculating the ratio of said test impedance to the lowest impedance associated with said frequency range to set the power level output by the frequency generator, and when said switch is in said second state, said frequency generator is coupled to said surgical instrument, so as to apply said electrical signal having a frequency that is associated with the lowest impedance and/or highest conductivity to the tissue.

It is yet another aspect of the present invention to provide a method of performing electrosurgery on tissue comprising the steps of providing a frequency generator and an impedance analyzer that are coupled to a controller, said frequency generator generating an electrical signal at a frequency greater that about 3 MHz; providing a surgical instrument that is electrically coupled to said frequency generator and said impedance analyzer; contacting the tissue with said surgical instrument; identifying the impedance of the tissue with said impedance analyzer over a range of associated frequencies; identifying a set frequency that reduces the impedance and/or increases conductivity of the tissue; adjusting the frequency of said electrical signal generated by said frequency generator to said set frequency; and applying said electrical signal to the tissue via the surgical instrument.

It is a further aspect of the present invention to provide a method of performing electrosurgery on tissue comprising the steps of providing a frequency generator and an impedance analyzer that are coupled to a controller storing a predetermined set impedance, said frequency generator generating an electrical signal; providing a surgical instrument that is electrically coupled to said frequency generator and said impedance analyzer; contacting the tissue with said surgical instrument; identifying the impedance of the tissue with said impedance analyzer over a range of associated frequencies; adjusting the frequency of said electrical signal generated by said frequency generator to obtain said set impedance; and applying said electrical signal at said frequency to the tissue via the surgical instrument.

It is another aspect of the present invention to provide a laparoscope comprising a hand grip operatively carrying a thumb trigger and a hand trigger; an elongated support shaft extending from said hand grip; a first actuation member slideably disposed within said support shaft, said first actuation member having opposed first and second ends with a cavity extending therebetween, said first end of said first actuation member attached to said hand trigger; at least two electrically-isolated grasping arms carried by said body and operatively attached with said second end of said actuation member, said at least two grasping arms configured to move between opened and closed positions; a connection interface electrically coupled to said at least two electrically-isolated grasping arms, said connection interface adapted to be connected to the electrostimulator; a second actuation member slideably disposed within said cavity, said second actuation member having opposed first and second ends, said first end of said second actuation member attached to said thumb trigger; and a cutting blade attached to said second end of said second actuation member and said support shaft, said cutting blade extending at least partially between said at least two grasping arms.

Yet still another aspect of the present invention is to provide a laparoscope comprising a hand grip operatively carrying a thumb trigger and a hand trigger; an elongated support shaft extending from said hand grip; a first actuation member slideably disposed within said support shaft, said first actuation member having opposed first and second ends with a cavity extending therebetween, said first end of said first actuation member attached to said hand trigger; at least two electrically-isolated grasping arms carried by said body and operatively attached with said second end of said actuation member, said at least two grasping arms configured to move between opened and closed positions; a connection interface electrically coupled to said at least two electrically-isolated grasping arms, said connection interface adapted to be connected to the electrostimulator; a second actuation member slideably disposed within said cavity, said second actuation member having opposed first and second ends, said first end of said second actuation member attached to said thumb trigger; and a scissor assembly attached to said second end of said second actuation member and said support shaft, said scissor assembly extending at least partially between said at least two grasping arms.

Another aspect of the present invention is to provide a variable-frequency stimulator for performing electrosurgery on tissue comprising a controller; a surgical instrument coupled to said controller and adapted to contact the tissue; and a frequency generator coupled to said controller and configured to supply an electrical signal to said surgical instrument, wherein when said frequency generator is coupled to said surgical instrument, so as to apply said electrical signal at a frequency greater than about 3 MHz to the tissue, thereby reducing the impedance and/or increasing the conductivity of the tissue.

BRIEF DESCRIPTION OF THE DRAWINGS

These and other features and advantages of the present invention will become better understood with regard to the following description, appended claims, and accompanying drawings wherein:

FIG. 2A is a perspective view of a fixture used to hold a plurality of thermocouples or thermistors in contact with the tissue surrounding a surgical site in accordance with the concepts of the present invention;

FIG. 2B is another perspective view of the fixture of FIG. 2A used to hold a plurality thermocouples in contact with the tissue surrounding the surgical site in accordance with the concepts of the present invention;

FIG. 3 is a schematic view of a four component Maxwell-Wagner tissue model;

FIG. 19 is a perspective view of an alternative laparoscope configured for use with the variable-frequency stimulator in accordance with the concepts of the present invention;

FIG. 20B is a perspective view of the grasping arms provided by the end effector of the alternative laparoscope configured for use with the variable-frequency stimulator with the scissor assembly removed in accordance with the concepts of the present invention;

DETAILED DESCRIPTION OF THE INVENTION

Figure 1:
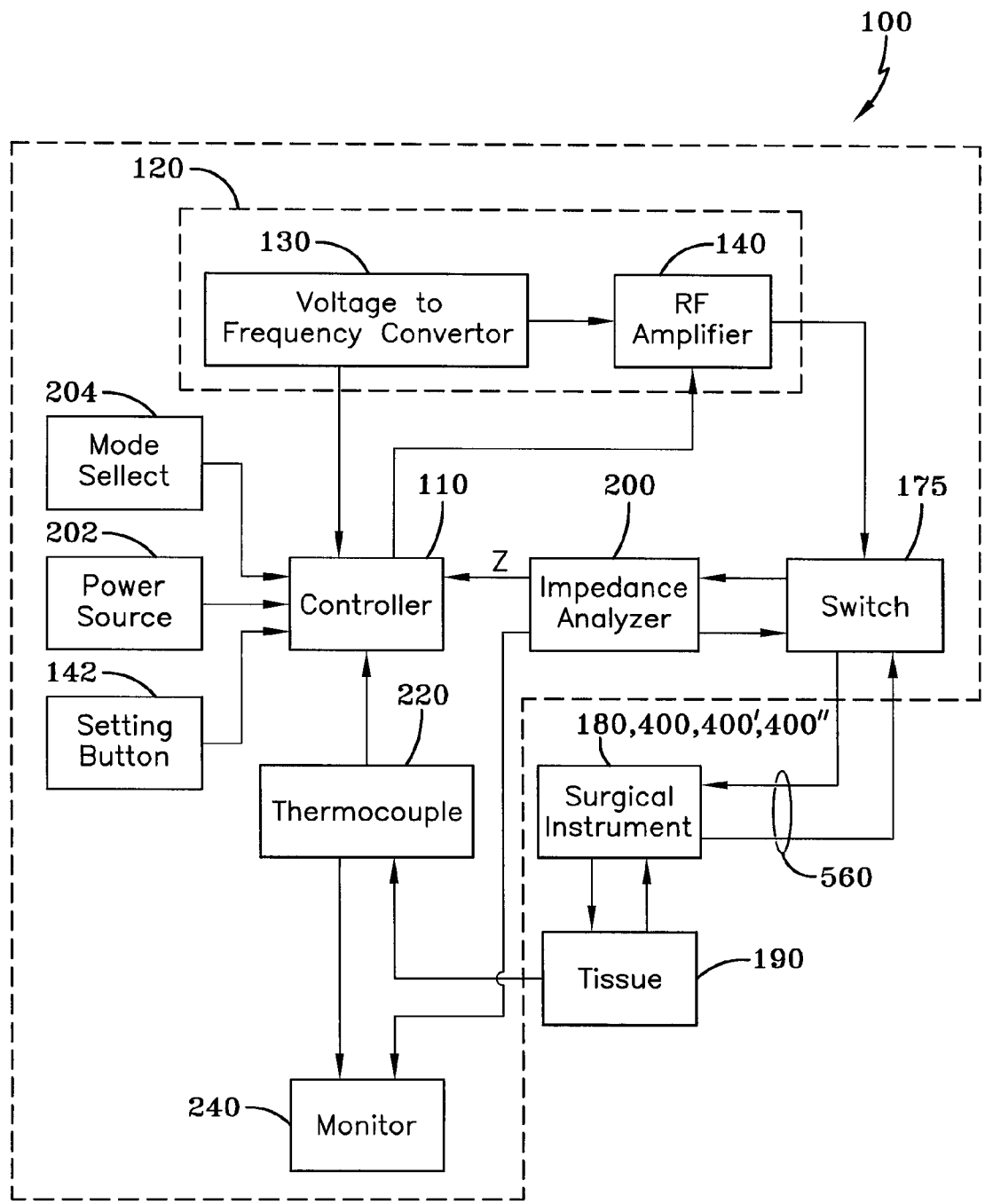
FIG. 1 is a block diagram of a variable-frequency stimulator in accordance with the concepts of the present invention.

A variable-frequency stimulator for electrosurgery is generally referred to by numeral 100, as shown in FIG. 1 of the drawings. Specifically, the variable-frequency stimulator 100 includes a controller 110 that provides the necessary hardware and/or software to carryout the functions of the variable-frequency stimulator 100 to be discussed. Coupled to the controller 110 is a stimulation frequency generator 120, which includes a voltage to frequency converter 130 that is coupled to an RF (radio frequency) amplifier 140. The voltage to frequency converter 130 is configured to convert a voltage signal received from the controller 110 into a signal having a predetermined frequency. For example, the voltage to frequency converter 130 may be configured to generate electrical signals having a variable frequency, such that a plurality of signals having different frequencies are generated over a frequency range. Alternatively, the frequency converter 130 may be configured to generate one signal at a fixed or discrete frequency, which does not vary over a range. For example, the voltage to frequency converter 130 may be configured to generate electrical signals at frequencies ranging between about 500 kHz to 250 MHz; ranging from about 3 MHz to 30 MHz, as well as ranging from about 500 kHz-20 GHz, although any other suitable frequency range may be used. Furthermore, it is contemplated that the voltage to frequency converter 130 may also be configured to generate electrical signals at a frequency range of any suitable increment or size. That is, the voltage to frequency converter 130 may generate signals over a range having a lower limit frequency of about 4 MHz to an upper limit frequency of any desired value (at any incremental divisions thereof), including but not limited to the upper limit frequencies of 5 MHz, 6 MHz, 7 MHz, 8 MHz, etc. . . . Furthermore, the signals generated by the voltage to frequency converter 130 having at a single frequency may utilize any desired frequency (at any incremental division thereof), such as frequencies of about 4 MHz and above for example. For example, frequencies of 5 MHz, 6 MHz, 7 MHz, 8 MHz, 9 MHz, etc. may be used. The RF amplifier 140, also coupled to the controller 110, is configured to increase the amplitude of the electrical signal generated by the voltage to frequency converter 130 to a level preprogrammed at the controller 110 or manually set via a setting button 142. The electrical signal output by the RF amplifier 140 having the desired frequency and amplitude characteristics is delivered to a switch 175 that is electrically coupled to a surgical instrument suitable for performing electrosurgery, such as a surgical instrument 180. The surgical instrument 180, which will be discussed in detail below, is a mechanical device, such as a laparoscope or tissue dissector for example, that is configured to perform various manipulations, including electrosurgical manipulations to biologic tissue, including but not limited to grasping, cutting, and cauterizing the tissue 190. It should be appreciated by those well practiced in the art that the frequency of stimulation need not be specified by a voltage to frequency converter, but that any suitable means can be used to specify the frequency of stimulation.

The variable-frequency stimulator 100 also in one exemplary embodiment includes an impedance analyzer 200 that is coupled to the controller 110 and to the switch 175. It should be appreciated that the switch 175 may comprise any suitable mechanical, electrical, or electromechanical switching device that is configured to electrically couple either the frequency generator 120 or the impedance analyzer 200 with the surgical instrument 180. Specifically, the impedance analyzer 200 is configured to identify the impedance or electrical conductivity of the tissue 190 that is being treated by the surgical instrument 180. As such, the impedance analyzer 200 is configured to generate a plurality of electrical signals each with a different frequency that are applied to the tissue 190 to identify the associated tissue 190 impedance. That is, the impedance analyzer 200 is configured to sweep through a range of frequencies that are applied to the tissue 190 when the instrument 180 is brought into contact with the tissue 190, and each associated impedance measurement is recorded by the controller 110. Furthermore, the impedance analyzer 200 is configured to monitor the impedance of the tissue 190 over any desired range of frequencies, including but not limited to a range of frequencies, such as from about 500 kHz to 250 MHz; 100 kHz to 250 MHz; 3 MHz to 30 MHz, as well as ranging from about 500 kHz-20 GHz, for example. The impedance data acquired by the impedance analyzer 200 is recorded or stored by controller 110 and is processed in a manner to be discussed to determine the particular stimulation frequency that is to be delivered from the stimulator 120 to the tissue 190 via the electrosurgical instrument 180.

Because the electrical conductivity of the tissue 190 is highly anisotropic and decreases when coagulated, it is important to frequently analyze the impedance of the tissue 190 by the frequency analyzer 200. Thus, by controlling the electrical impedance of the tissue 190 being treated by variable-frequency electrical stimulation, less collateral damage will be inadvertently imposed upon surrounding biological tissue 190 due to a reduction in operating temperature. This is because the power dissipated by conductive elements can be described by $P=VI=I^2Z=V^2/Z$, where P is power, V is voltage, I is electrical current, and Z is the impedance of the element.

The variable-frequency stimulator 100 may be powered by any suitable AC (Alternating Current) or DC (Direct Current) power source 202, such as a battery or standard wall outlet that is coupled to the controller 110. Furthermore, a mode-select or setting switch 204 may be coupled to the controller 110 to place the variable-frequency stimulator 100 into various operating states or modes to be discussed below.

In one aspect, the variable-frequency stimulator 100 may be configured such that the control algorithm utilized by the controller 110 is programmed in MATLAB/Simulink using a real-time Windows target kernel and a control loop sample frequency of 1 kHz. In addition, the controller 110 may include a PCI-6221 (National Instruments) data acquisition card used to sample tissue temperature, voltage, and electrical current data in a manner to be discussed. In one aspect, the PCI-6221 data acquisition card may have two analog voltage outputs, whereby the first output is sent to the voltage-to-frequency converter 130 that is used to convert the variable voltage command signal from MATLAB/Simulink into a variable frequency. The second analog output from the controller will be sent to the high-bandwidth voltage controlled variable gain amplifier that will be used to adjust the gain of the signal sent to an RF amplifier 140 and then subsequently to the tissue grasped by the instrument 180. In another aspect, the impedance analyzer 200 may comprise an 4294A impedance analyzer, which is used to measure the electrical frequency response of the tissue 190 that is in contact with the electrosurgical instrument 180 over a broad frequency range, as previously discussed.

In addition, the variable-frequency stimulator 100 may also include a plurality of temperature sensors 220, such as a thermocouple or thermistor, that is attached to the tissue 190 and that is configured to monitor the temperature of the tissue 180 that surrounds the surgical site in which the surgeon is using the electrosurgical instrument 180. The temperature identified by the temperature sensor 220 is delivered to the controller 110 and/or to a display monitor 240, such as an LCD (liquid crystal display), for example. By allowing the surgeon to monitor the temperature of the tissue 190 via the display 240, he or she is able to determine whether tissue 190 that is near to the region that is being treated by the electrosurgical instrument 180 is exceeding a threshold temperature and is in danger of being damaged. In one aspect, the controller 110 may utilize the temperature of the tissue 190 in order to vary the duty cycle and/or the frequency of the electrical current signal that is generated by the frequency generator 120. This allows the surgeon to have better control of the function of the electrical stimulation applied by the tissue dissector, in the case of coagulation or cutting of tissue for example. It is also contemplated that the output of the impedance analyzer 200 may be coupled to the monitor 240 as well, to allow the surgeon to view the impedance of the tissue 190 being treated.

In one aspect, the temperature sensor 220 used to measure the temperature of the tissue 190, may comprise five FLUKE 5611A silicon-bead probe thermocouples 220 that are carried by a polycarbonate fixture 242, as shown in FIGS. 2A-B, which includes a slot that is dimensioned to receive various end-effectors of the electrosurgical instruments 180, including those discussed in detail below. Specifically, the thermocouples or temperature sensors 220 may be placed in the fixture 242 at a 1 mm distance around a mouth 244, which is dimensioned to receive the surgical instrument 180 to measure the temperature distribution profile during the surgical procedures. The fixture 242 also includes a spring clip mechanism 246 that allows the thermocouple device 220 to be removeably clipped to the tissue 190, such that when the tissue 190 is subsequently stimulated by the variable-frequency stimulator 100, the nearby tissue temperature is measured by the five thermocouples 220. It should also be appreciated by those well practiced in the art that the tissue temperature could be measured by any suitable sensor such as an infrared sensor.

Thus, with the components of the variable-frequency stimulator 100 set forth, the following discussion sets forth the operational steps carried out by the variable-frequency stimulator 100 during its operation. Initially, before the tissue 190 is grasped with the surgical instrument 180, the switch 175 is placed in a first mode or state, where the impedance analyzer 200 is electrically coupled to the surgical instrument 180. Specifically, the impedance measured by the impedance analyzer 200 across the grasping arms of the surgical instrument 180 before they contact the tissue 190 is infinite, and when the tissue 190 is brought into contact or grasped with the instrument 180 the impedance becomes finite and the impedance analyzer 120 sweeps through a predetermined range of frequencies, as previously discussed. In one aspect, the sweep time of the impedance analyzer 200 over the range of frequencies may be achieved in less than 100 ms, for example, although other sweep times may be used. The impedance analyzer 200 continues analyzing the impedance of the tissue 190 over the predetermined frequency range until the surgeon activates the electrical stimulation function of the stimulator 100 by placing the switch 175 into a second mode or state. Placing the switch 175 into the second mode or state disconnects the impedance analyzer 200 from the surgical instrument 180, and connects the frequency generator 120 to the surgical instrument 180, thereby allowing electrical signals at a range of frequencies to be delivered to the surgical site as previously discussed. The impedance of the tissue can be determined while the tissue is stimulated through the ratio of the measured voltage and current.

In another aspect, the variable-frequency stimulator 100 may be configured to be placed in various operating modes via the mode-select switch 204. Specifically, in a first or normal mode, the variable-frequency stimulator 100 utilizes a control algorithm that is executed by the controller 110, which is programmed to deliver electrical signals over a range of stimulation frequencies, as previously discussed, which have a constant average power that produces a lower or the lowest level of tissue impedance over a specific frequency band. This allows the electrosurgical instrument 180 to have a fast cutting time, while allowing the temperature of the tissue 190 to remain low thereby reducing burns and collateral damage to the tissue. Specifically in one aspect, the tissue impedance at a stimulation frequency of about 500 kHz is compared by the controller 110 to the lowest tissue impedance measured over an entire predetermined frequency range, such as from about 100 kHz to 4 MHz or from about 300 kHz to 250 MHz, as determined by the impedance analyzer 200, as previously discussed. Next, the ratio of the tissue impedance at 500 kHz with respect to a lower or the lowest measured impedance is calculated by the controller 110 in order to reduce the power level of the electrical stimulation, which would be implemented at the frequency producing the lowest tissue impedance. The frequency of stimulation can also be chosen without use of an impedance analyzer to reduce tissue impedance or increase tissue conductivity based on the knowledge that tissue conductivity increases in general with increasing stimulation frequency, in particular with stimulation frequencies greater than 3 MHz. It should also be clear that the frequency of stimulation corresponding to a lower or the lowest level of tissue impedance can be used without any reduction in power. It should also be clear that after a stimulation frequency in the range of, for example, 3 MHz-20 GHz is used, a lower frequency of stimulation for example between 300 kHz-3 MHz could be subsequently used. It should also be clear that the frequency and/or duty cycle of stimulation can be adjusted based on tissue temperature feedback to produce lower or more desirable operating temperatures. This algorithm produces less collateral damage, necrosis and operating temperatures that are lower than that produced by currently available constant frequency stimulators that typically operate between 300 kHz and 3 MHz. The frequency of electrical stimulation that would most closely produce the desired tissue impedance or conductivity is then used with a constant average power stimulation mode each time the tissue 190 is subsequently grasped by the instrument 180.

In a second operating mode selected by the mode-select switch 204, the electrostimulator 100 maximizes the conductivity of the tissue 190, by selecting a stimulating frequency from the range of analyzed stimulation frequencies that achieves a lower or the lowest tissue impedance, as identified by the impedance analyzer 200. That is, the controller 110 utilizes the stimulation frequency and associated impedance data that is collected by the impedance analyzer 200 to control the voltage to frequency converter 130 and RF amplifier 140 of the frequency generator 120, so as to generate a stimulation frequency that is applied to the tissue 190 that reduces or minimizes the impedance or increases or maximizes the conductivity of the tissue 190. The reduction and/or minimization in impedance and/or the increase and/or maximization of conductivity is with respect to the levels of impedance and/or conductivity that can be obtained with lower frequency levels between for example 300 kHz 3 MHz. As such, the present invention is capable of lowering or reducing the impedance with respect to the impedance levels that can be obtained by commercially available devices that operate between 300 kHz-3 MHz, which is highly desirable.

In a third operating mode selected by the mode-select switch 204, the controller 110 is configured to control the stimulating frequency such that the impedance of the grasped tissue is the same regardless of the type of tissue 190 being treated by the instrument 180. This normalized operation of the variable-frequency electrostimulator 100 allows the surgeon or other operator of the device to have a consistent level of cutting and/or cauterizing control across all types of tissue. This is in contrast to the electrostimulator 100 operating modes previously discussed, which may vary the stimulation frequency to provide a lower or the lowest impedance depending on the type of tissue 190 being treated. That is, by configuring the electrostimulator 100 to select the necessary frequency to achieve the same level of impedance and/or conductivity independent of the type of tissue 190 allows the surgeon to apply a consistent ratio of current to voltage for any specific power setting used to treat the tissue 190, regardless of the type of tissue or the way that the a specific type of tissue is grasped. This ensures that consistent tissue heating effects occur regardless of the tissue that is treated.

In a fourth operating mode, any number of components from FIG. 1 may be omitted and a single electrical signal having a constant or fixed frequency of stimulation, as previously discussed, can be applied to the tissue with or without any feedback controller. In this embodiment, the specific frequency of stimulation can be specified ahead of time anywhere between a range of any desired frequencies, such as for example 4 MHz 20 GHz. This can be done to reduce collateral damage, tissue temperature and burning during electrosurgery, because the tissue impedance decreases in general with increasing stimulation frequency. The tissue conductivity also increases in general with increasing stimulation frequency. These two factors significantly impact the ratio of voltage to current for any power level that is used to cut tissue which in turn impacts the tissue temperature, collateral damage and tissue burning. The reduction and/or minimization in impedance and/or the increase and/or maximization of conductivity with respect to the levels of impedance and/or conductivity that can be obtained with lower frequency levels between for example 300 kHz-3 MHz.

Thus, because most biological tissue impedances decrease with increasing stimulation frequency, control over the tissue impedance is possible through the control of the stimulation frequency via the variable-frequency stimulator 100. As such, the stimulator 100 is configured to stimulate tissue with a frequency that reduces and/or minimizes the electrical impedance of the tissue. Hence, the stimulator 100 is also configured to stimulate tissue with a frequency that increases and/or maximizes the electrical conductivity of the tissue. Such reduction and/or minimization of the electrical impedance of biological tissue treated by the stimulator 100 is able to reduce the operating temperatures of surrounding tissue to prevent or reduce the amount of collateral damage and tissue necrosis that occurs during electrosurgical procedures. It should also be appreciated that the variable-frequency stimulator 100, through control of the frequency of stimulation can also control the amount and/or rate of blood loss, tissue temperature, tissue cauterization, and tissue burning that occurs during electrosurgery, which is highly desirable.

Experimental

Figure 4:
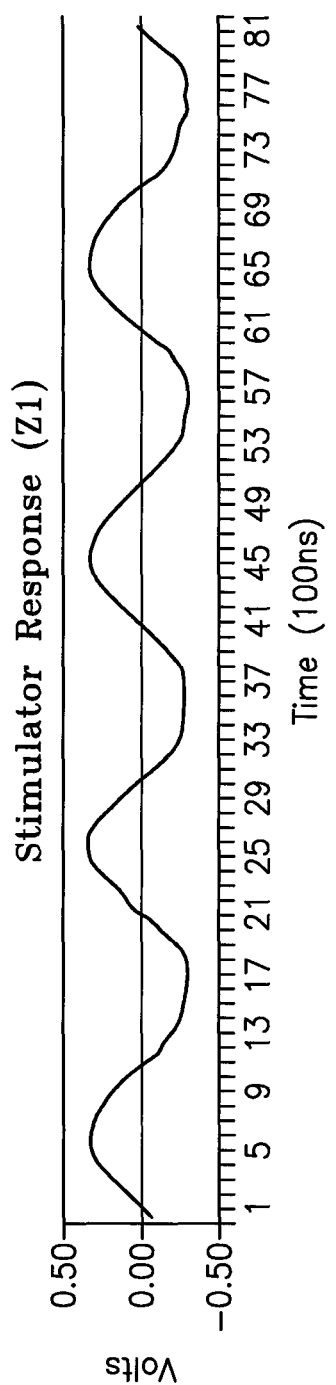
FIG. 4 is a graph showing the response of the tissue model of FIG. 3 across impedance Z1.
Figure 5:
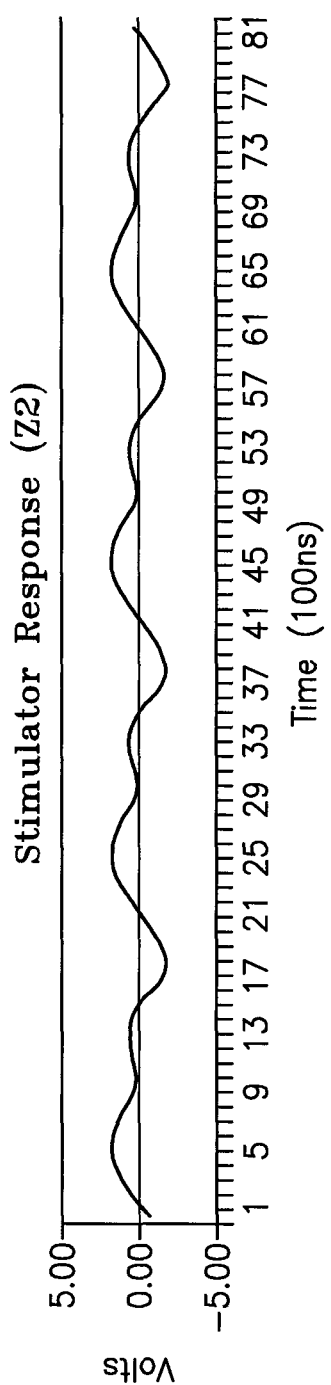
FIG. 5 is a graph showing the response of the of the tissue model of FIG. 3 across impedance Z2.

To evaluate the efficacy of the methods of electrical stimulation utilized by the electrostimulator 100, a four component Maxwell-Wagner model of tissue 300, as shown in FIG. 3 was experimentally evaluated with an electrosurgical stimulator, using an electrosurgical instrument comprising bipolar laparoscope forceps. The default stimulation frequency was set at a constant 500 kHz, while a power setting of 1 W was used. Two different combinations of resistor and capacitor values were chosen to show how the constant frequency affects the voltage across the tissue model 300. As shown in FIG. 4, the peak-to-peak voltage applied by the stimulator is roughly 0.6V for resistors and capacitors ($R_1$-$R_2$ and $C_1$-$C_2$) having an effective impedance of Z1. However, for different values of resistance and capacitance ($R_1$-$R_2$ and $C_1$-$C_2$) with an effective impedance of Z2, the peak-to-peak voltage stimulator increases to roughly 3.5V, as shown in FIG. 5.

Figure 6:
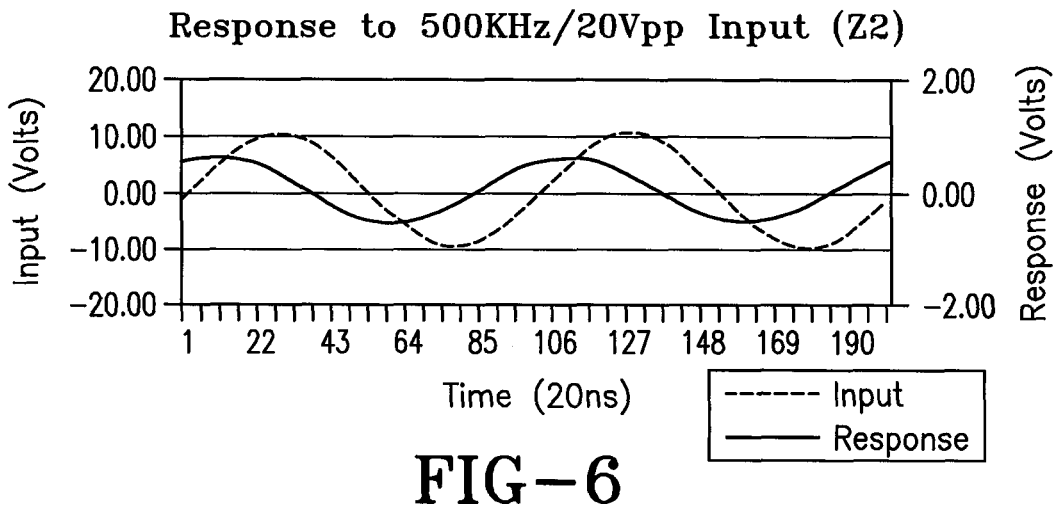
FIG. 6 is a graph showing the input and output response of a 500 kHz stimulation frequency across impedance Z2 of the tissue model of FIG. 3, where the peak-to-peak voltage of the response is 1.0V.
Figure 7:
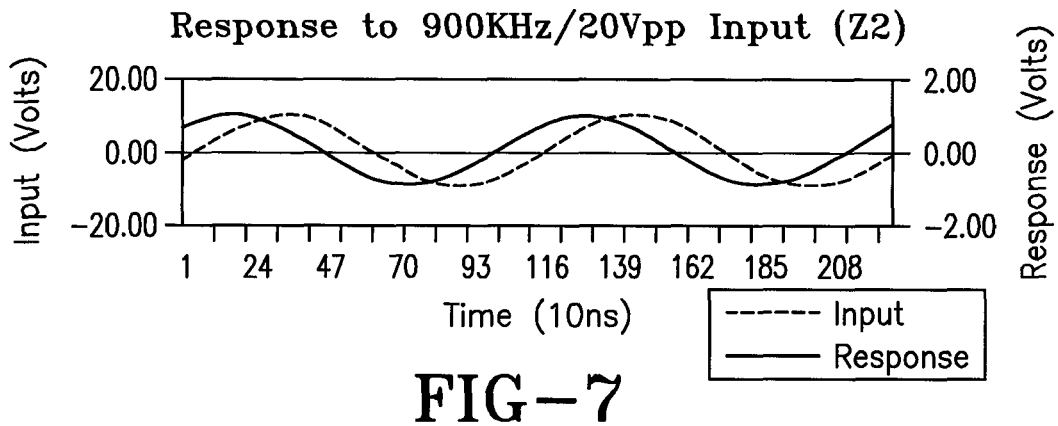
FIG. 7 is a graph showing the input and output response of a 900 kHz stimulation frequency across the impedance Z2 of the tissue model of FIG. 3, where the peak-to-peak voltage of the response 2.0V.
Figure 8:
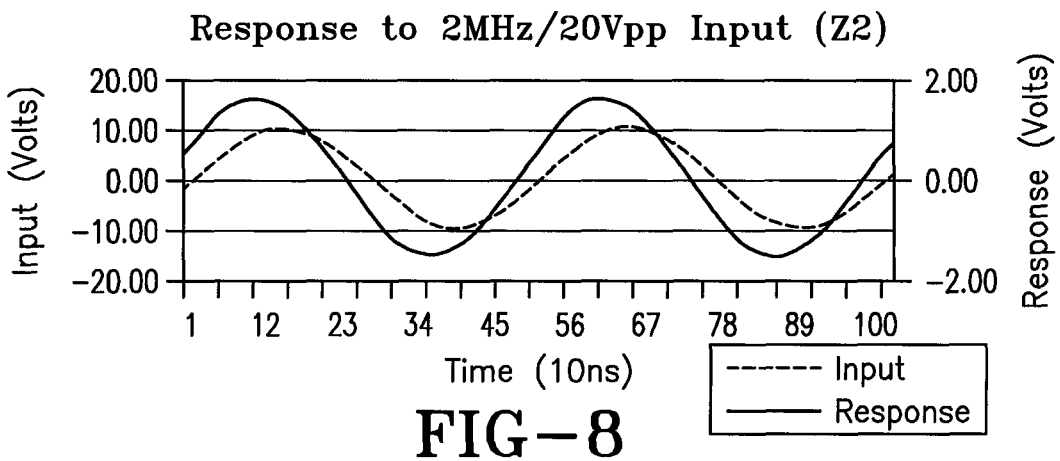
FIG. 8 in a graph showing the input and output response of a 2 MHz stimulation frequency across the impedance Z2 of the tissue model of FIG. 3, where the peak-to-peak voltage of the response is 2.6V.

In the next evaluation, a function generator was used to stimulate the tissue model (Z2) at three different frequencies to show the advantage of using a variable stimulation frequency to allow the effective impedance of the tissue to be lowered. As shown from the stimulation frequencies at 900 kHz and 2 MHz, the voltage across the tissue model 300 is much larger compared to the input voltage than at the 500 kHz stimulation frequency, as shown in FIGS. 6, 7, and 8. Specifically, FIG. 6 shows the response of the voltage across impedance Z2 with a stimulation frequency of 500 kHz; FIG. 7 shows the increased amplitude in the voltage across impedance Z2 when the stimulation frequency was increased to 900 kHz, even though the input amplitude is the same; FIG. 8 shows the increased amplitude in the voltage across impedance Z2 when the stimulation frequency is increased to 2 MHz. Thus, variation of the stimulation frequency changes the amplitude of the voltage applied across impedance Z2.

Thus, the results set forth above show that the same amount of electrical current can be driven through the biological tissue 190 with a lower voltage when a stimulation frequency is chosen to minimize and/or reduce the effective impedance of the tissue 190. During electrosurgery, this results in lower operating temperatures, and therefore less collateral damage to surrounding tissue. Furthermore, the results above also show that for any specified electric power level, a plurality of different ratios of voltage to current can be achieved by choice of the frequency of stimulation to control the impedance of the biological tissue 190. This is important because of the different tissue heating effects that occur with different ratios of voltage and current. Specifically, the temperature increase in the tissue from electrical stimulation is described by Eq. 1, where $$\Delta T = \frac{J^2 t}{\sigma C_P d},$$

where J is the electric current density, t is the amount of time the tissue is stimulated, $\sigma$ is the electrical conductivity; $C_P$ is the specific heat of the tissue, and d is the density of the tissue.

Therefore, when the stimulation frequency is selected to increase and/or maximize the tissue conductivity, the amount of time to cut the tissue is reduced, and the temperature of the tissue 190 will increase if a constant power stimulation mode is utilized. However, if the cutting time and all other parameters, except a, remain constant, a lower tissue temperature increase is achieved.

Figure 9:
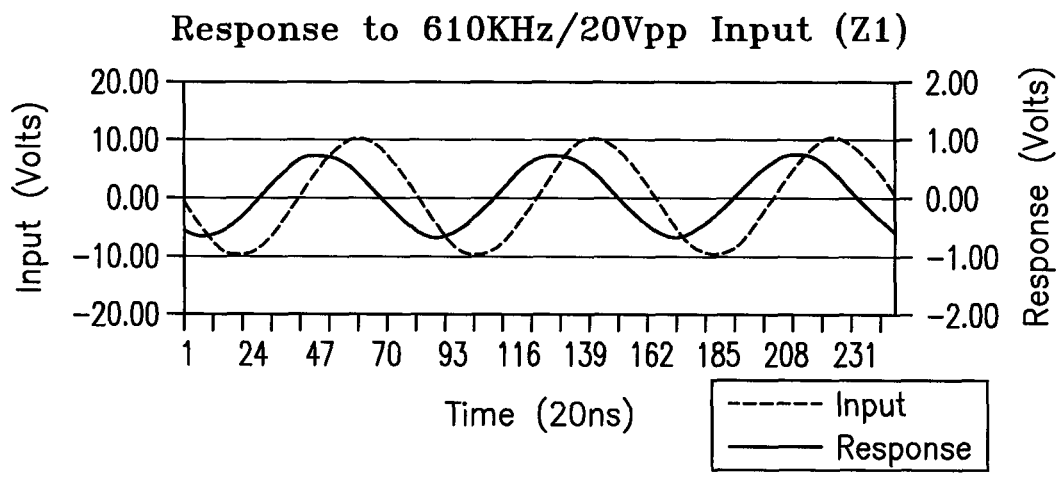
FIG. 9 is graph showing the input and output response to a 610 kHz stimulation frequency across impedance Z2, where the peak-to-peak voltage of the response is 1.5V.
Figure 10:
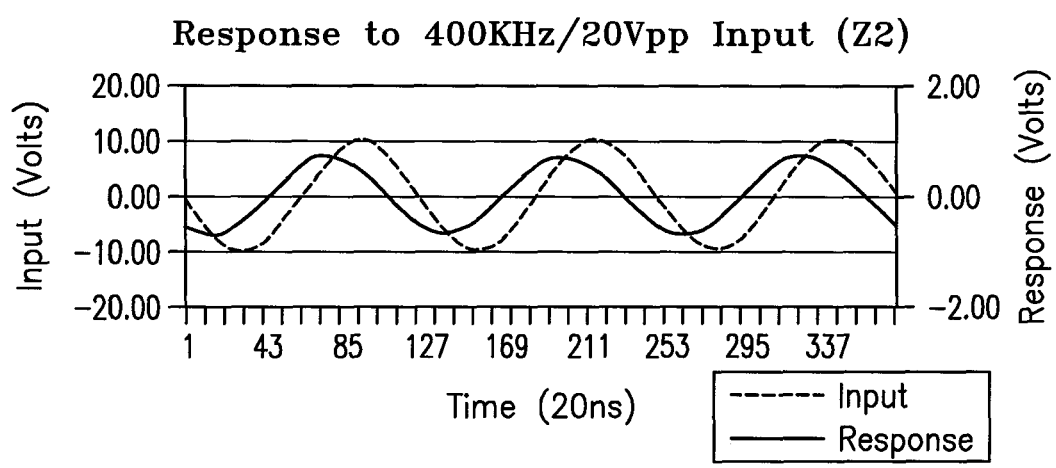
FIG. 10 is a graph showing the input and output response to a 400 kHz stimulation frequency across impedance Z2, where the peak-to-peak voltage of the response is 1.5V.

In addition, during the third mode of operation of the electrostimulator 100, impedances Z1 and Z2 of the model 300 are each stimulated at different frequencies. In the first case, impedance Z1 is stimulated with a peak-to-peak input of 20V and a frequency of 610 kHz, which resulted in a response of 1.5V peak-to-peak, as shown in FIG. 9. Next, impedance Z2 was stimulated with the same peak-to-peak input of 20V, but at a frequency of 400 kHz, which also resulted in a response of 1.5V peak-to-peak, as shown in FIG. 10. Thus, by choosing the appropriate stimulation frequency, the tissue impedance can be changed so that the voltage/current ratio can be kept the same. Thus, the current density through the tissue will remain constant and the heating of the tissue 190 described by Eq. 1 will be the same regardless of the type of tissue that is stimulated.

Figure 11A:
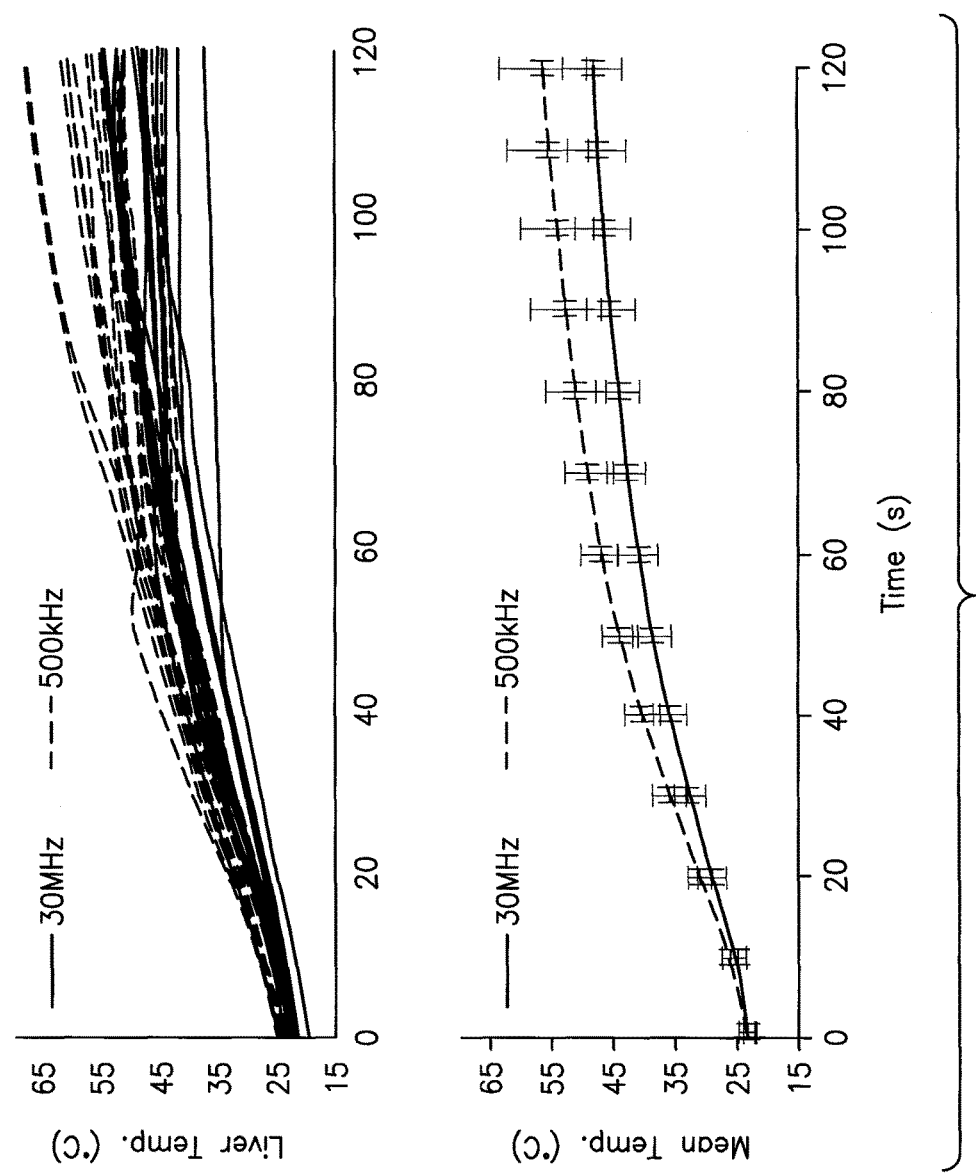
FIG. 11A is a graph showing the temperature measurements for liver tissue for 50 kHz and 30 MHz stimulation frequencies with a constant 15 W power setting.
Figure 11B:
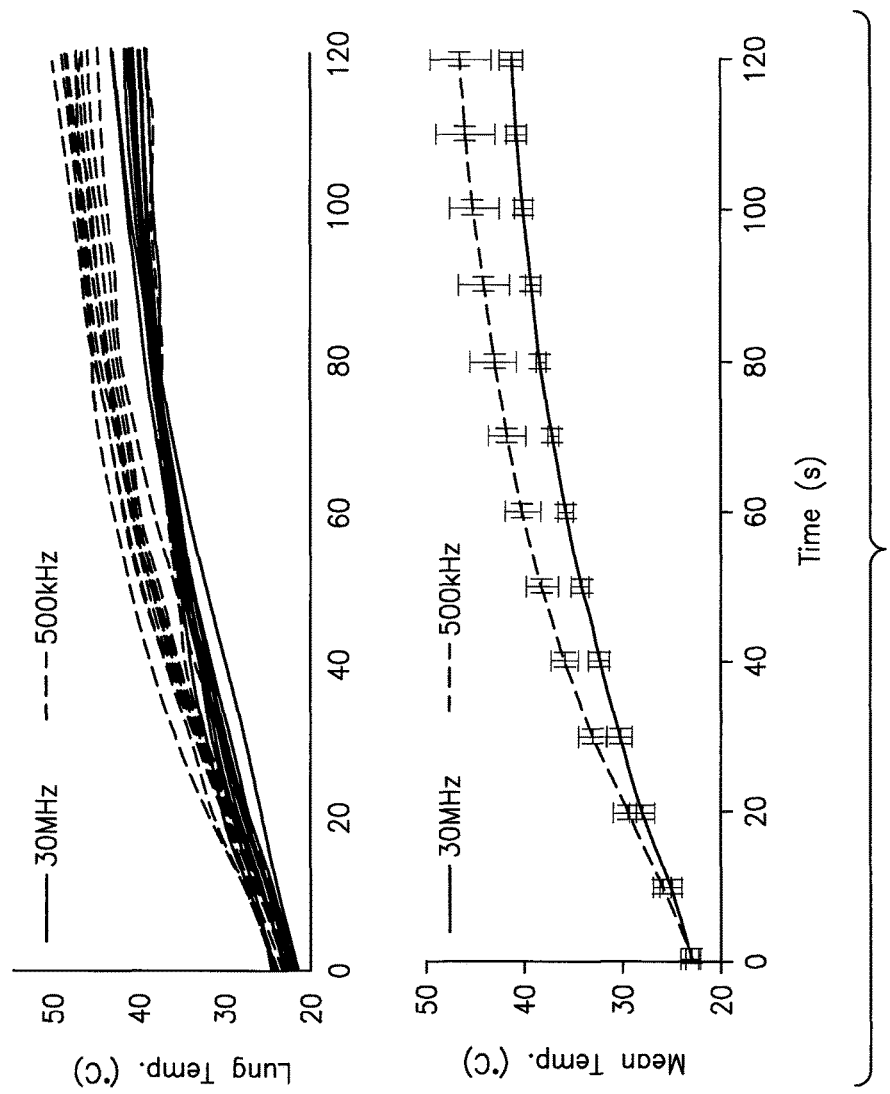
FIG. 11B is a graph showing the temperature measurements for lung tissue for 500 kHz and 30 MHz stimulation frequencies with a constant 10 W power setting.
Figure 11C:
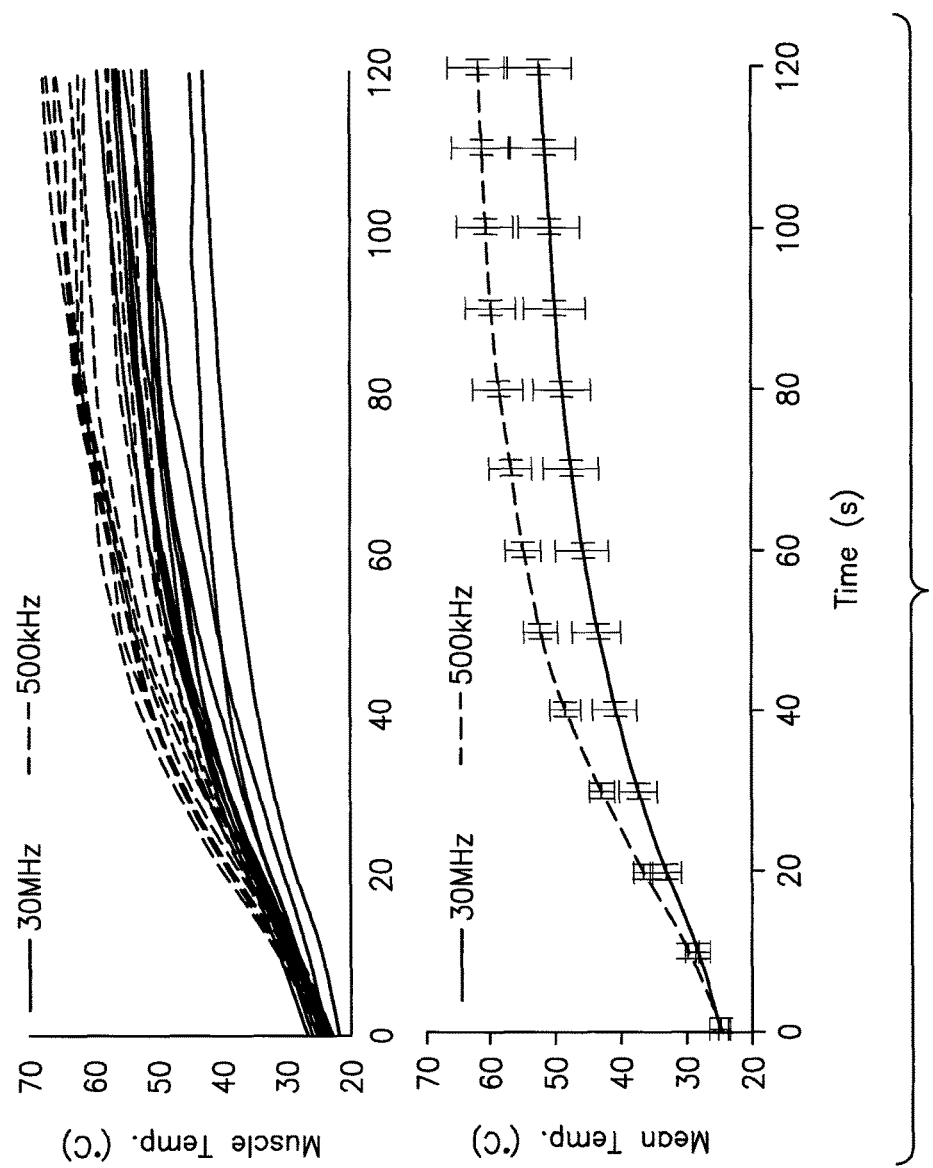
FIG. 11C is a graph showing the temperature measurements for muscle tissue for 500 kHz and 30 MHz simulation frequencies with a constant 15 W power setting.
Figure 12:
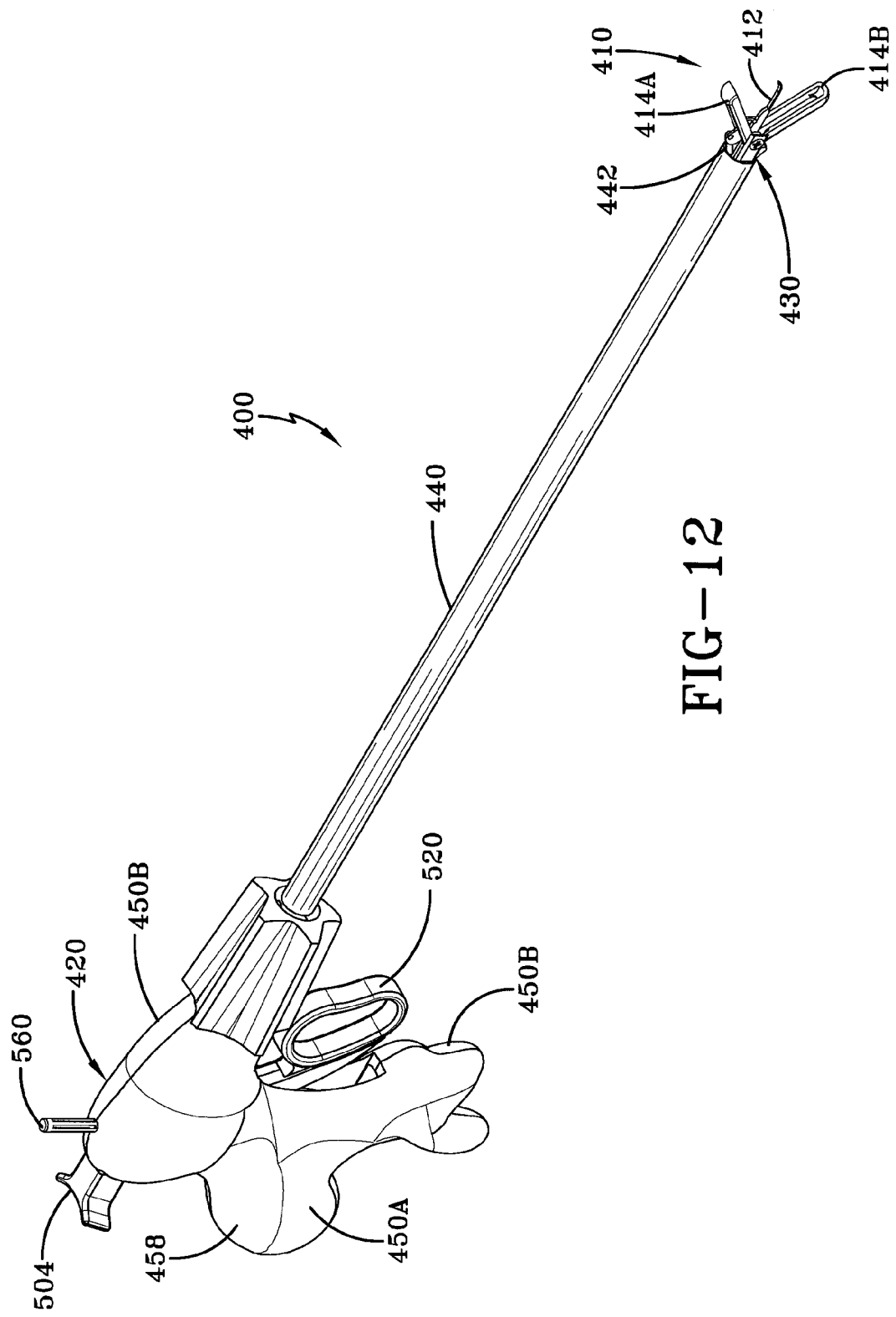
FIG. 12 is a perspective view of a laparoscope configured for use with the variable-frequency stimulator of FIG. 1 in accordance with the concepts of the present invention.
Figure 13:
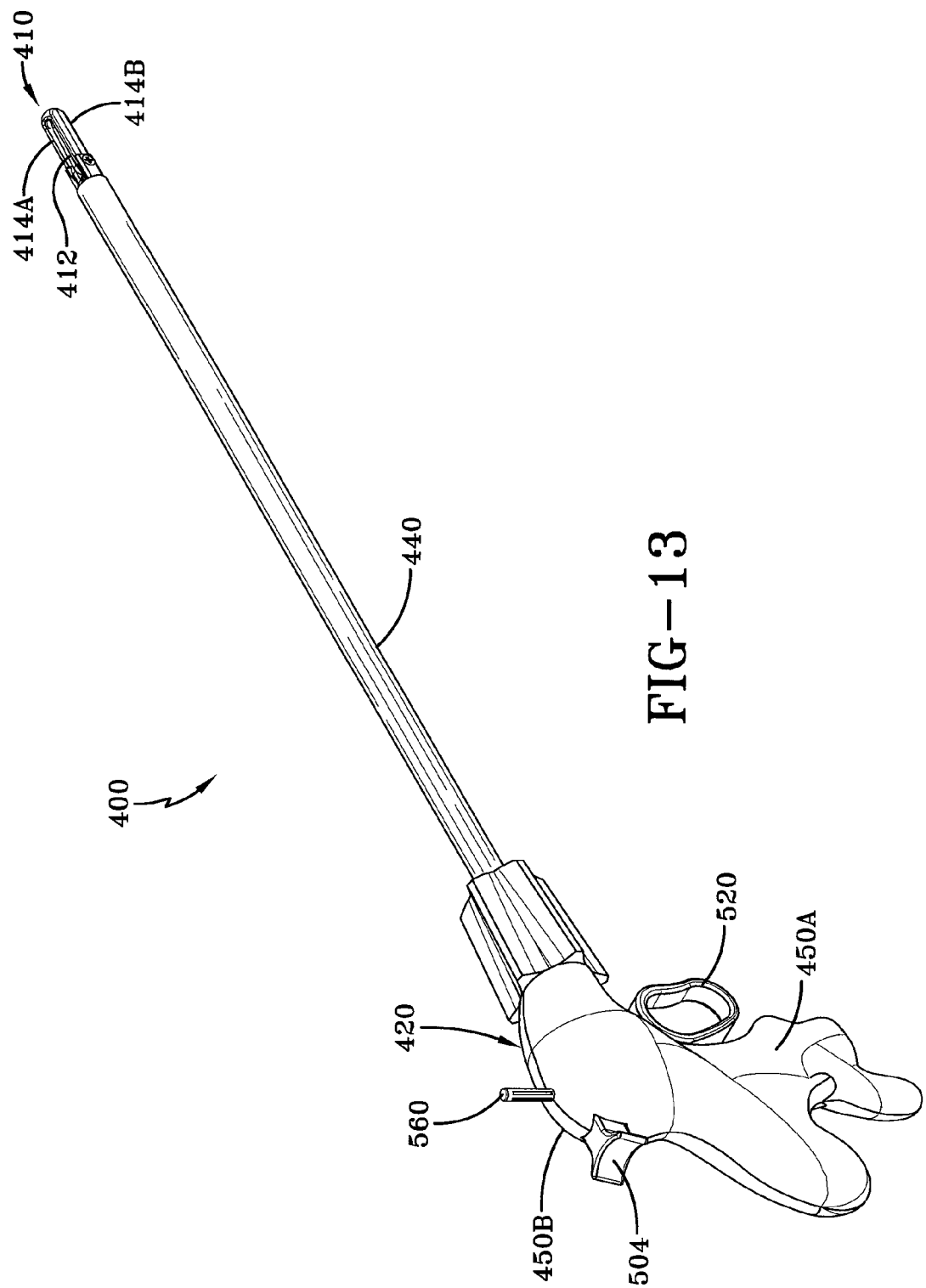
FIG. 13 is another perspective view of the laparoscope configured for use with the variable-frequency stimulator in accordance with the concepts of the present invention.
Figure 14A:
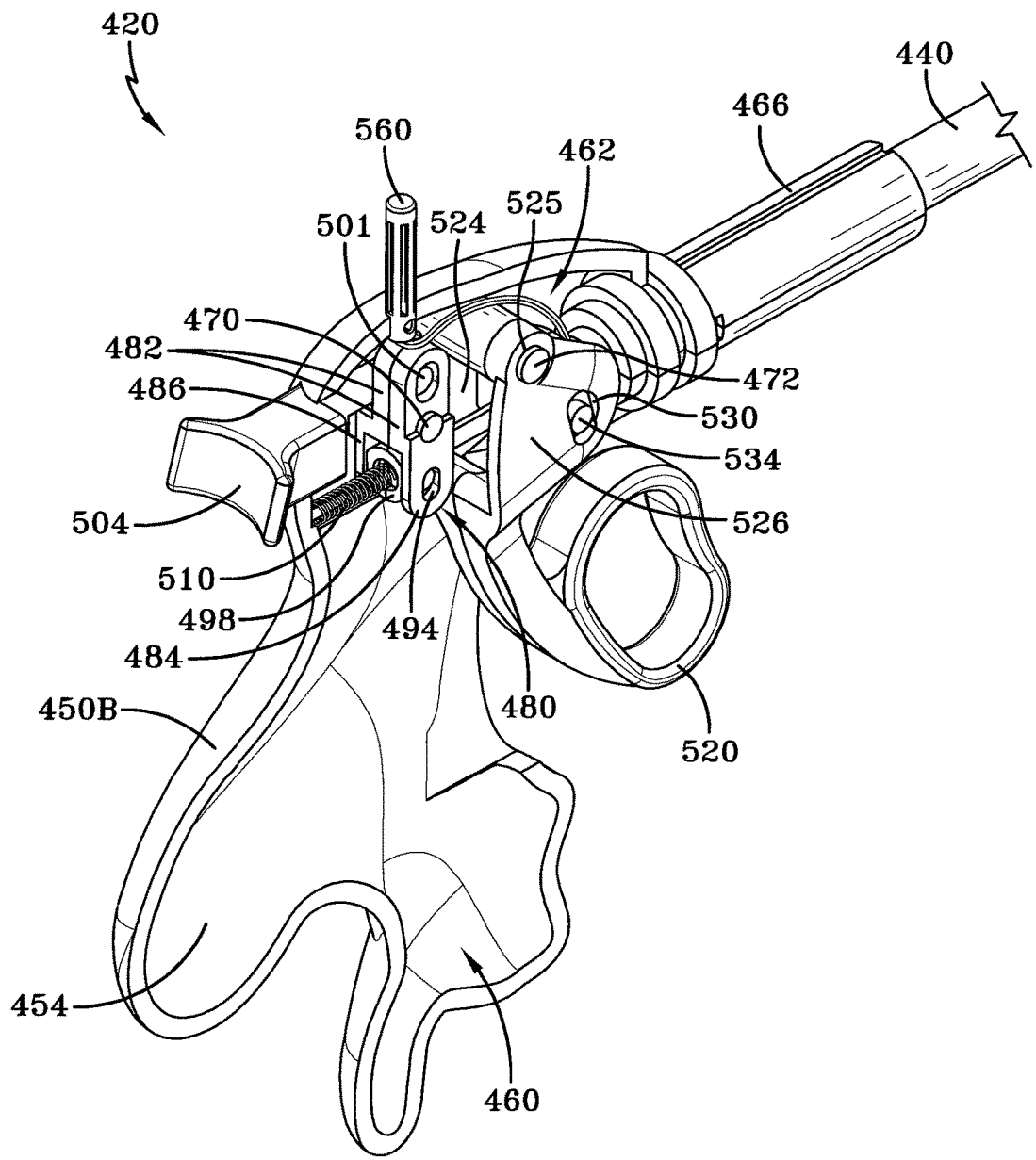
FIGS. 14A-D are perspective views of a hand grip provided by the laparoscope configured for use with the variable-frequency stimulator in accordance with the concepts of the present invention.
Figure 14B:
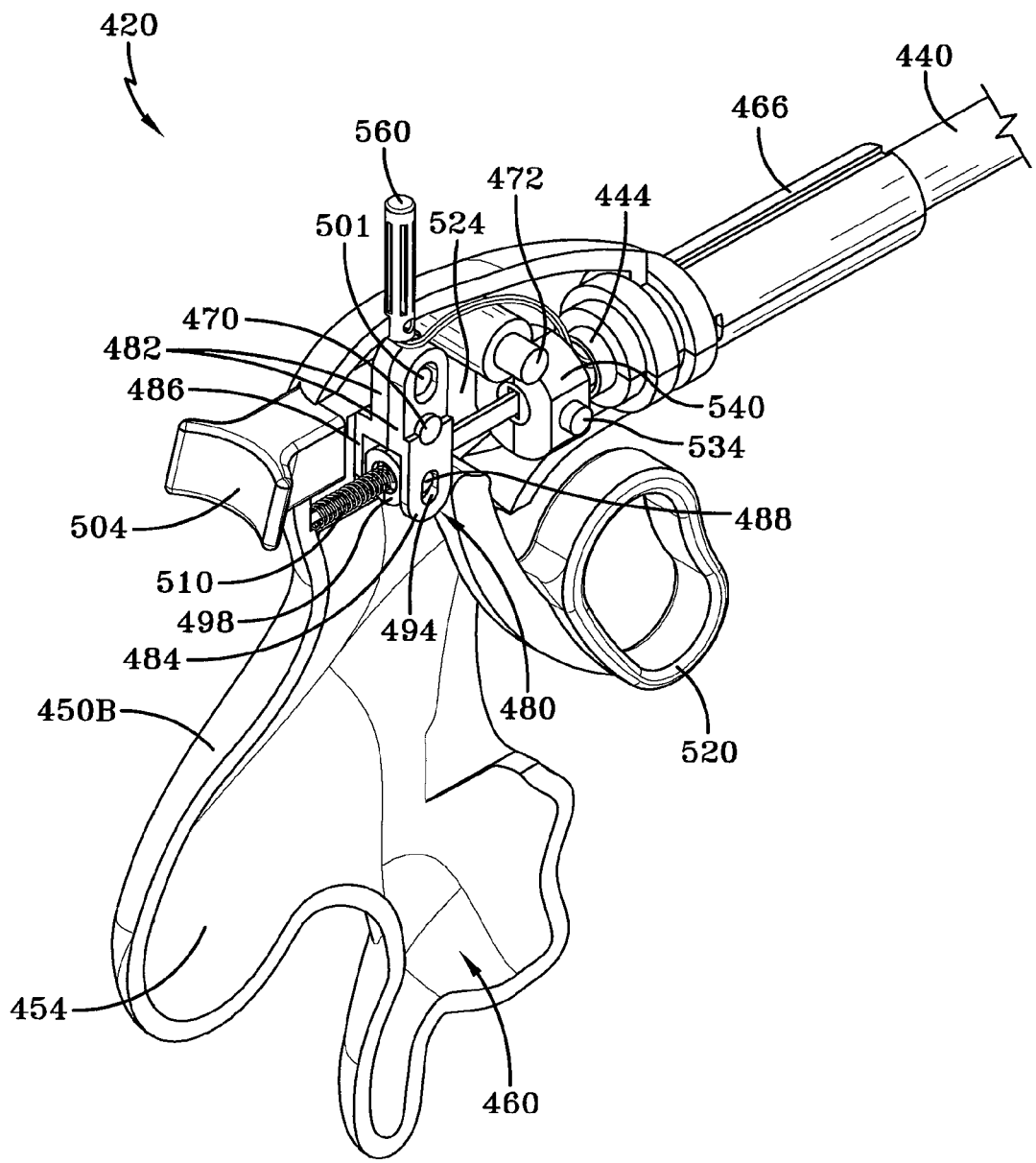
Figure 14C:
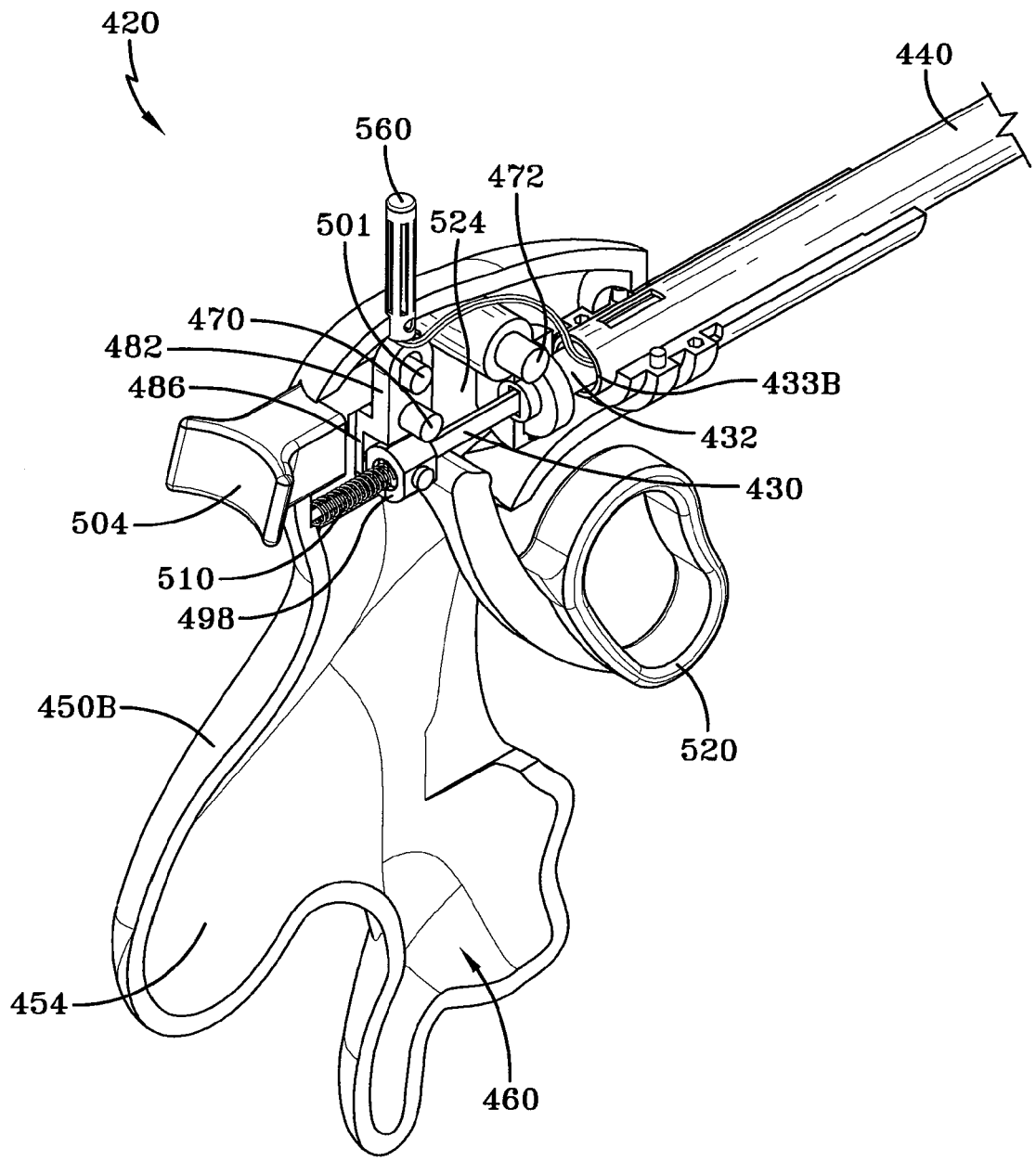
Figure 14D:
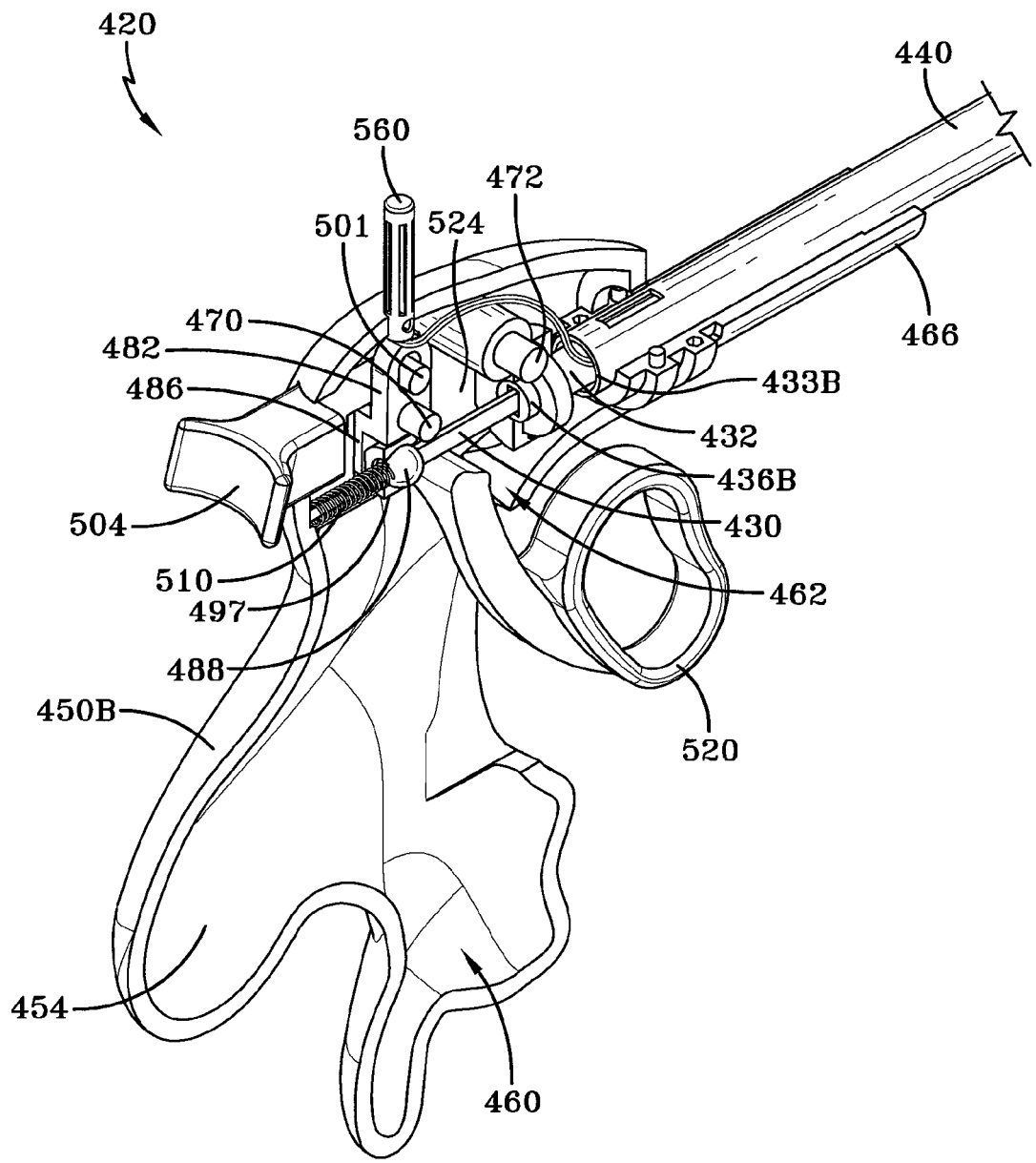

In addition, FIGS. 11A-C show temperature measurements in liver, lung, and muscle tissue when stimulating frequencies of 500 kHz and 30 MHz are used, as well as the average temperature of the tissue and corresponding standard deviation. It should be noted that the 30 MHz stimulation frequency produces a lower average temperature, with all three types of tissue, as shown in the Figs. For example, FIG. 11A shows the temperature measurements for liver tissue for 500 kHz and 30 MHz stimulation frequencies with a constant 15 W power setting, whereby the 30 MHz stimulation frequency produces a lower average tissue temperature. FIG. 11B shows the temperature measurements for lung tissue for 500 kHz and 30 MHz stimulation frequencies with a constant 10 W power setting, whereby the 30 MHz stimulation frequency produces a lower average tissue temperature. Finally, FIG. 11C shows the temperature measurements for muscle tissue for 500 kHz and 30 MHz simulation frequencies with a constant 15 W power setting, whereby the 30 MHz stimulation frequency produces a lower average tissue temperature. Thus, the 30 MHz stimulation frequency produced a 14%, 11%, and 15% lower average maximum tissue temperature in the respective liver, lung, and muscle tissue than the 500 kHz stimulation frequency produced.

Thus, with the discussion of the components and manner of operation of the variable-frequency stimulation device 100 set forth, the following discussion presents the various surgical instruments 180 that may be utilized with the stimulation device 100. Specifically, the surgical instrument 180 may comprise a laparoscope 400, as shown in FIGS. 12-18 of the drawings. Specifically, the laparoscope 400 comprises an end effector 410 having a cutter or cutting blade 412 and grasping arms 414A-B that are operatively attached to a hand grip 420 via actuation members 430 and 432 that extend through an elongated cavity 434 disposed in an elongated support shaft 440 having opposed ends 433A and 433B. Specifically, the actuation members 430 and 432 have respective opposed ends 434A-B and 436A-B, such that ends 434A,436A are operatively attached to the end effector 410 (cutting blade 412 and grasping arms 414A-B) and ends 434B,436B are operatively attached to the handgrip 420. The actuation member 432 slideably reciprocates within the cavity 434 of the support shaft 440, and includes an elongated receiving cavity 447 in which the actuation member 430 slideably reciprocates. That is, the actuation member 432 slideably reciprocates within the cavity 434 of the support shaft 440, while the actuation member 430 slideably reciprocates within the cavity 447 of the actuation member 432. Specifically, the hand grip 420, shown clearly in FIGS. 14A-D, is formed as a pair of opposed case sections 450A and 450B. The case sections 450A-B have an opposed inner surface 454 and outer surface 458, such that when the housing sections 450A-B are attached together, a cavity 460 is formed therein to carry an actuation assembly 462 that controls the operation of the end effector 410.

The hand grip 420 is attached to the support shaft 440 via a collar 466. In addition, the hand grip 420 also includes a pair of spaced pivot shafts 470 and 472 that extend from the inner surface 454 of the housing section 450B at a substantially right angle. A yoke member 480 is pivotably attached to pivot shaft 470 via mounting aperture 481. The yoke member 480 includes a pivot arm 482 that is attached to a pair of parallel spaced yoke arms 484 and 486, whereby a pivot aperture 490 is disposed in the pivot arm 482, and yoke apertures 494 are disposed in each yoke arm 484,486. It should be appreciated that the yoke member 480 may be formed as a single section or formed from two sections, as shown in the Figs. In addition, the spaced yoke arms 484,486 are configured to retain a clamp 497 that includes protrusions 488 that are received within the yoke apertures 494. The clamp 497 is attached to an end cap 498 that is attached at end 434B of the actuation member 430. In addition, a thumb trigger 504 is pivotably attached to the pivot aperture 490 of the yoke member 480 by a protrusion 501. Furthermore, the yoke member 480 is biased by a spring 510 that is disposed between the end cap 498 and the inner surface 454 of the rear of the hand grip 450B. Thus, when the thumb trigger 504 is depressed from its normal resting position, the spring 510 is compressed and the cutting blade 412 attached to end 434A of the actuation member 430 is retracted within the support shaft 440, and when the thumb trigger 504 is released, the spring 510 decompresses, causing the yoke member 480 to pivot, such that the cutter 412 to extends to its normal position.

The actuation assembly 462 also includes a hand trigger 520, as shown clearly in FIGS. 14A-D, which include a pivot aperture 524 that receives the protrusion 472 extending from the inner surface 454 of the case 450B therein, so as to allow the hand trigger 500 to pivot. The hand trigger 520 also includes spaced plates 524 and 526, each of which includes a receiving aperture 530 therein. The receiving apertures 530 are configured to pivotably receive protrusions 534 therethrough, which extends from an actuator clamp 540. The actuator clamp 540 is configured to be attached to the end 436B of an actuation member 432 that extends through the support shaft 440.

Thus, when the hand trigger 520 is squeezed or pulled backward from its normal resting position, a back edge 550 of the hand trigger 520 engages the yoke members 480, causing the cutter 412 to retract and the spring 510 to compress and the cutting blade 412 to retract, and the grasping arms 414A-B attached to the end 436A of the actuation member 432 to close. And when the hand trigger 520 is released, the spring 510 decompresses, such that the cutting blade extends forward and the grasping arms 414A-B open. Thus, due to the configuration of the thumb trigger 504 and the hand trigger 520, the cutter 412 and the grasping arms 414A-B are able to operate independently of one another.

In addition, the hand grip 420 also includes an electrical connection interface 560, such as a plug or port that is configured to electrically selectively couple the laparoscope end effector 410 to the switch 175 of the electrosurgical device 100.

Figure 15:
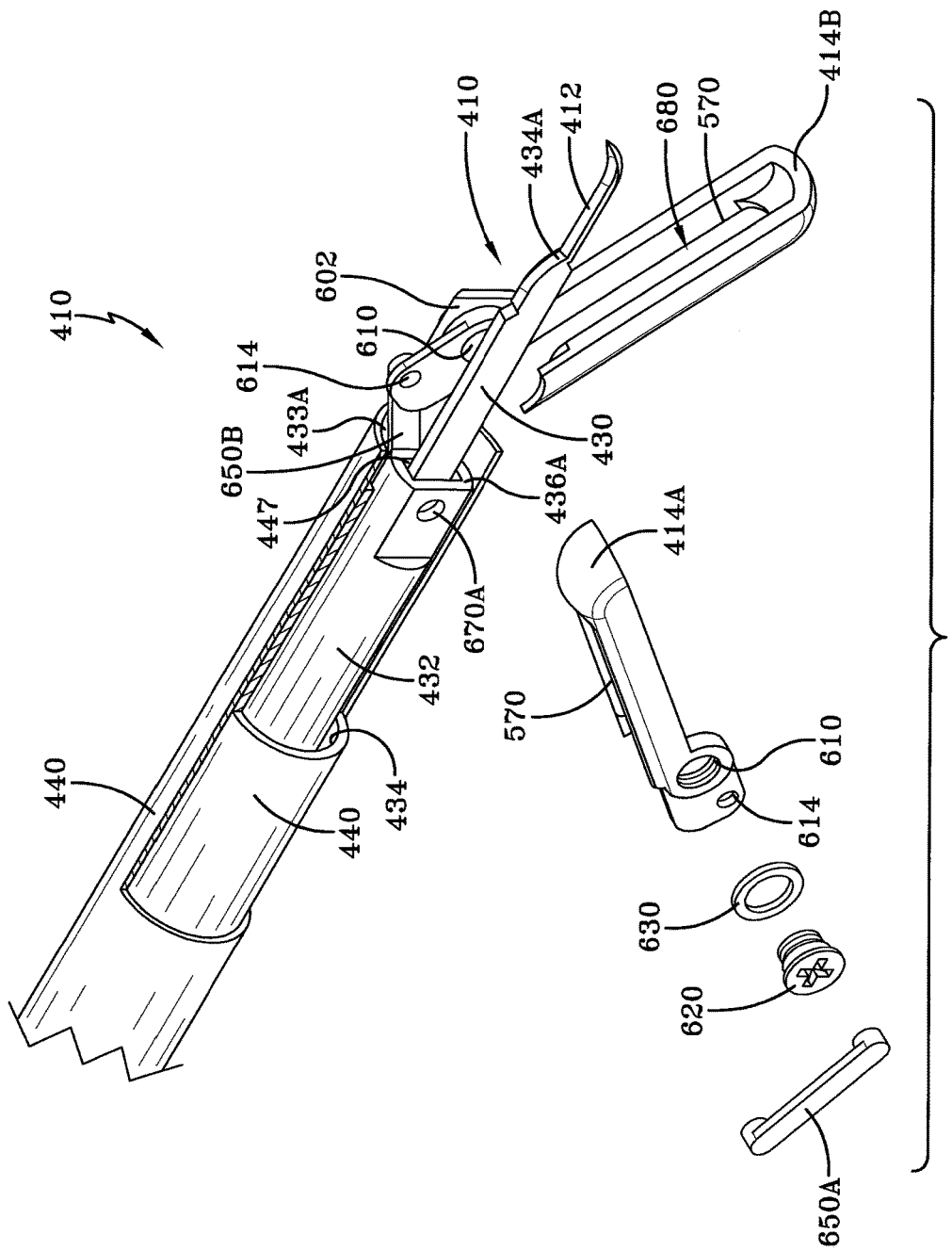
FIG. 15 is a partial exploded view of an end effector provided by the laparoscope configured for use with the variable-frequency stimulator in accordance with the concepts of the present invention.
Figure 16:
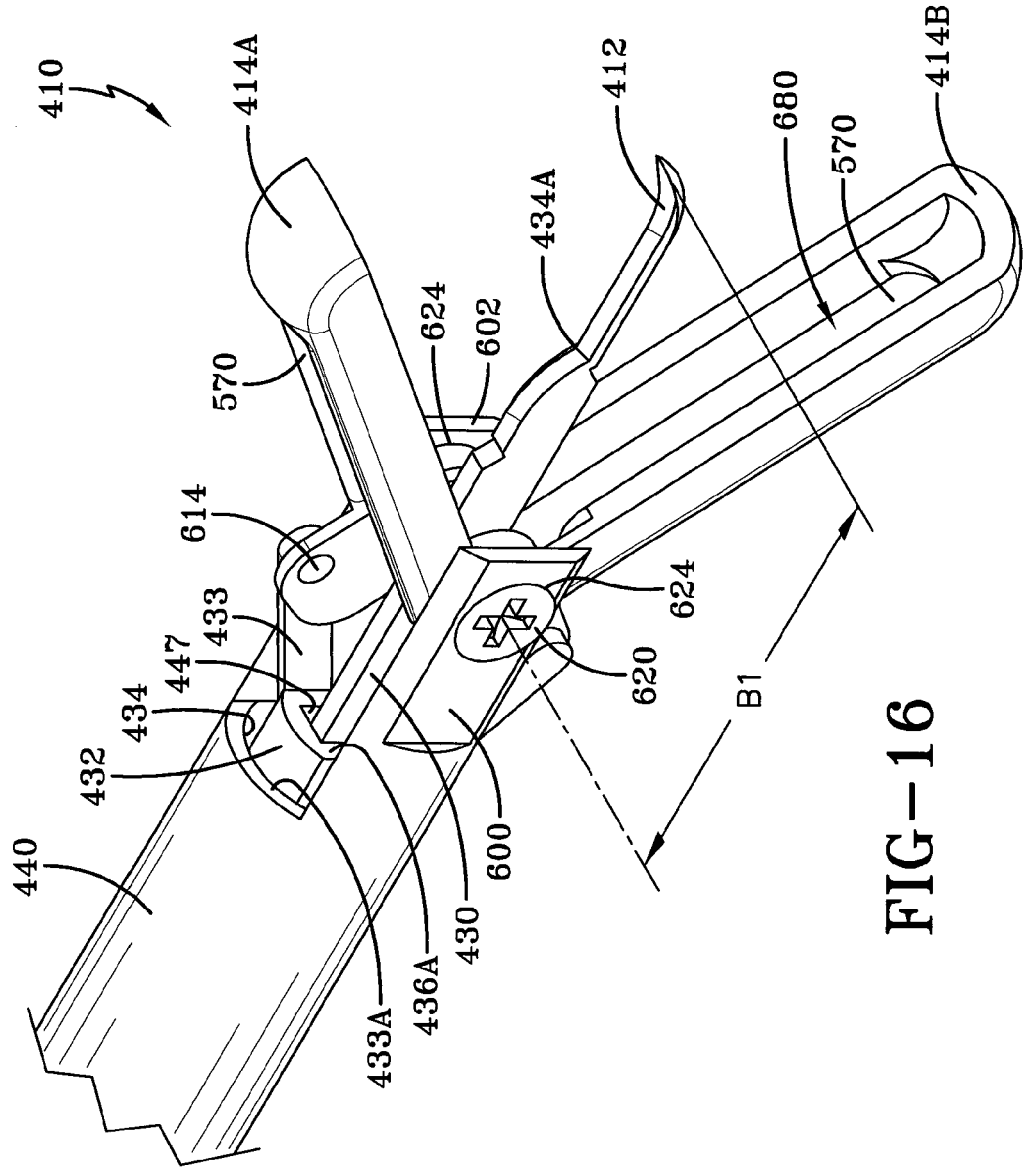
FIG. 16 is a perspective view of the end effector provided by the laparoscope configured for use with the variable-frequency stimulator in accordance with the concepts of the present invention.
Figure 17:
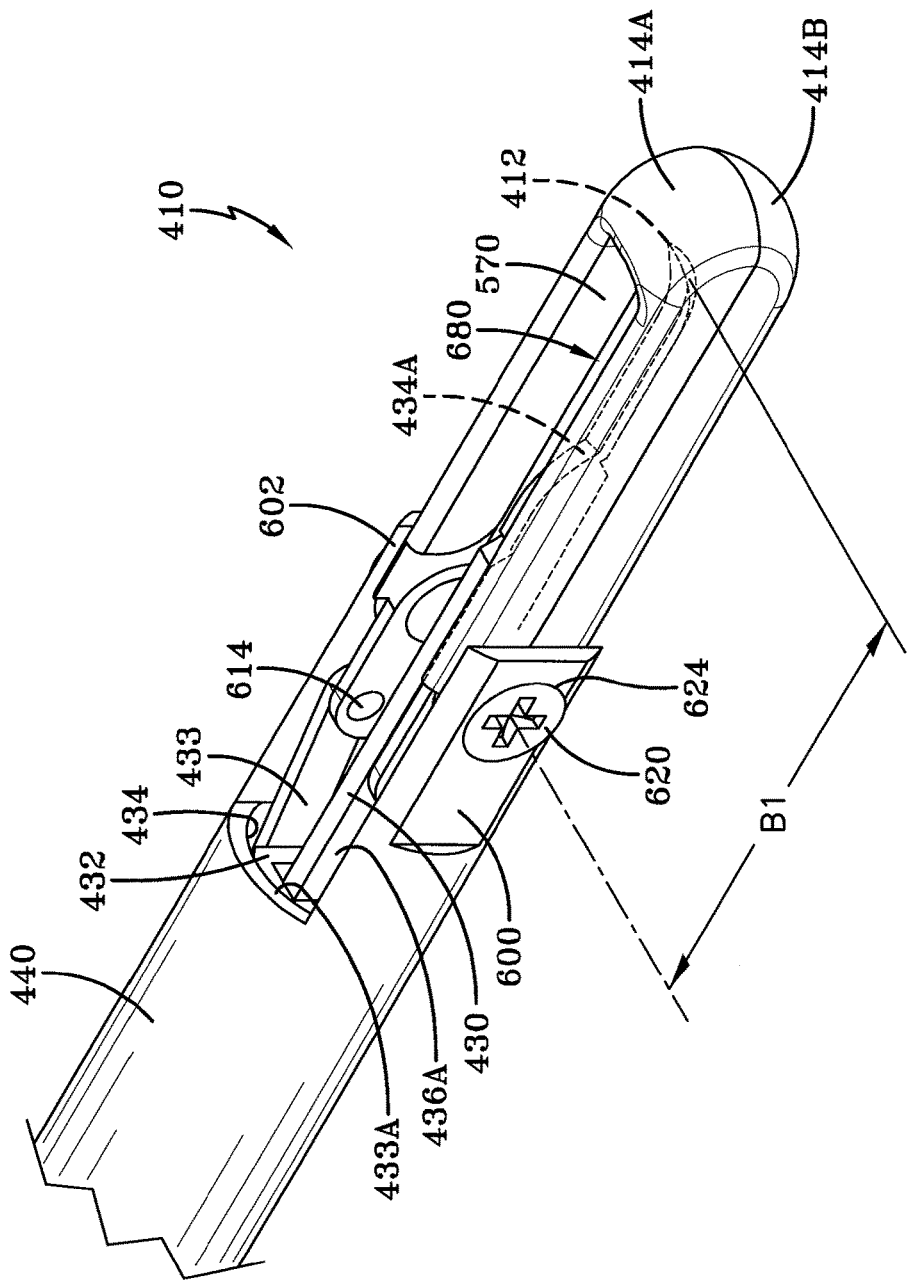
FIG. 17 is another perspective view of the end effector provided by the laparoscope configured for use with the variable-frequency stimulator in accordance with the concepts of the present invention.

Continuing to FIGS. 15-17, the pair of elongated grasping arms 414A-B of the end effector 410 each includes elongated apertures 570, as well as a pivot aperture 610 and an actuation aperture 614. As such, the grasping arms 414A and 414B are pivotably attached to respective attachment arms 600 and 602 that extend from the end 433A of the support shaft 440 by a suitable fasteners 620, such as a screw, that are received through the corresponding pivot apertures 610 and threadably retained in a fastener aperture 624 of the corresponding attachment arm 600 and 602. That is, the grasping arm 414A is pivotably attached to attachment arm 600 and grasping arm 414B is pivotably attached to attachment arm 602. In addition, dielectric bushings 630 are disposed between each fastener 620 and the inner circumference of the fastener aperture 624, so as to electrically isolate each grasping arm 414A and 414B from each other. In addition, wires 626 and 628 are respectively coupled at one end to the grasping arms 414A-B, and at another end to the connection interface 560.

In order to move the grasping arms 414A-B from an opened position to a closed position, the actuation member 432 includes pivot apertures 670A-B that are disposed proximate to the end 436A. Specifically, the pivot apertures 670A-B of the actuation member 432 are attached to respective grasping arms 414A-B by corresponding linkage members 650A-B. That is, linkage member 650A is pivotably attached between pivot aperture 614 of grasping arm 414A and pivot aperture 670A of the actuation member 432, and linkage member 650B is pivotably attached between pivot aperture 614 of grasping arm 414B and pivot aperture 670B of the actuation member 432. As such, when the connection interface 560 is electrically coupled to the switch 175, the variable-frequency stimulator 100 is electrically coupled to the grasping arms 414A-B. Furthermore, to allow the grasping arms 414A-B to be electrically isolated from each other, the pivot apertures 670A-B of the actuation member 432 may be electrically isolated from the linkage arms 650A-B by dielectric bushings 630, or alternatively, the linkage arms 650A-B may be formed from non-conductive dielectric material.

The cutting blade or cutter 412 provided by the laparoscope 400 is attached to the end 434A of the actuation member 430. Specifically, the cutting blade 412 is configured to extend within a gap or cavity 680 formed between the grasping arms 414A-B, whereby they are closed. Furthermore, the actuation member 430 to which the cutter 412 is attached is disposed within the cavity 447 of the actuation member 432 and is configured to reciprocate back and fourth by the operation of the thumb trigger 504 of the hand grip 420 previously discussed.

Figure 18A:
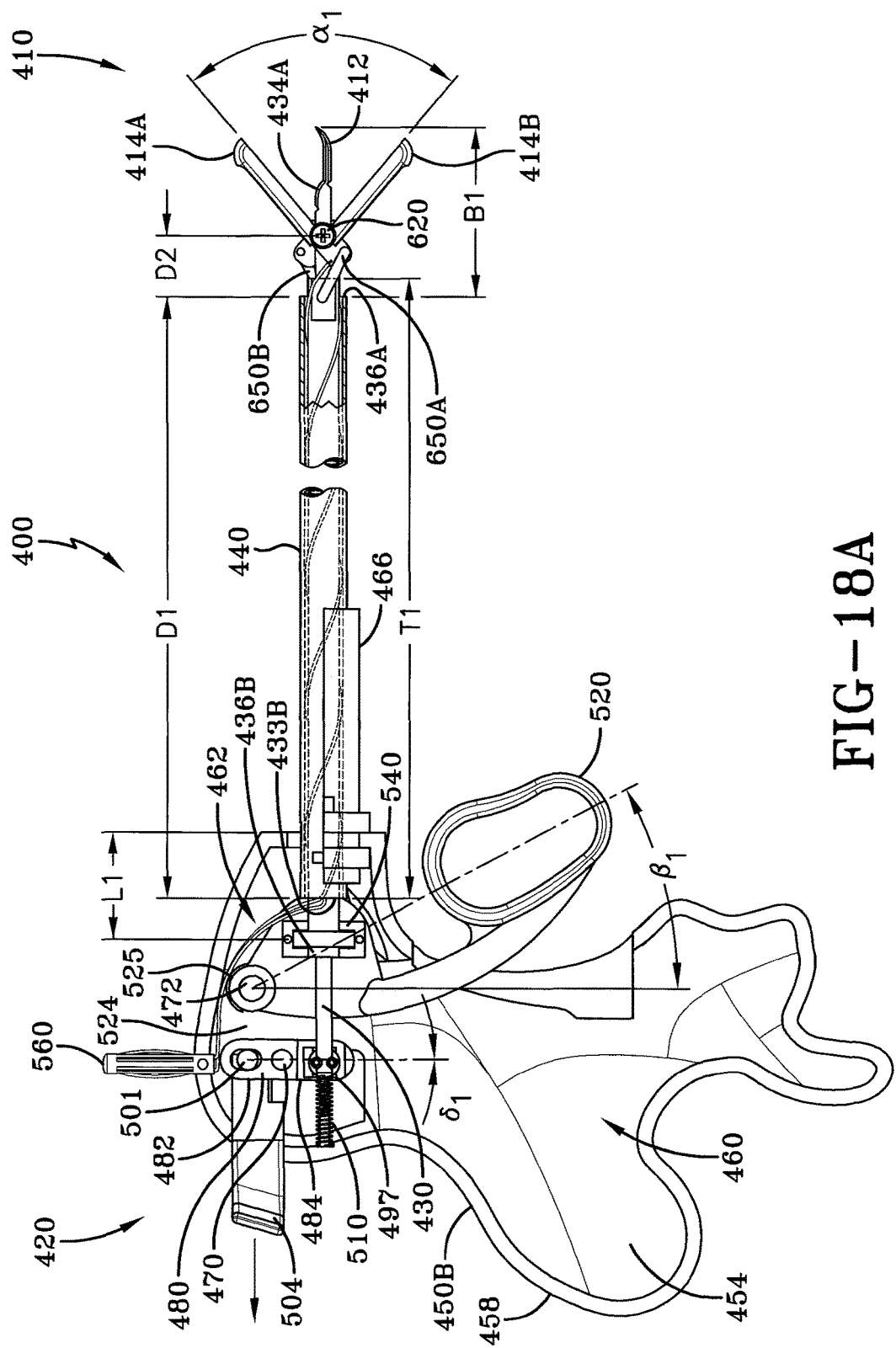
FIGS. 18A-D are elevational views of the laparoscope configured for use with the variable-frequency stimulator showing the operation of the laparoscope when a thumb trigger and a hand trigger are actuated in accordance with the concepts of the present invention.
Figure 18B:
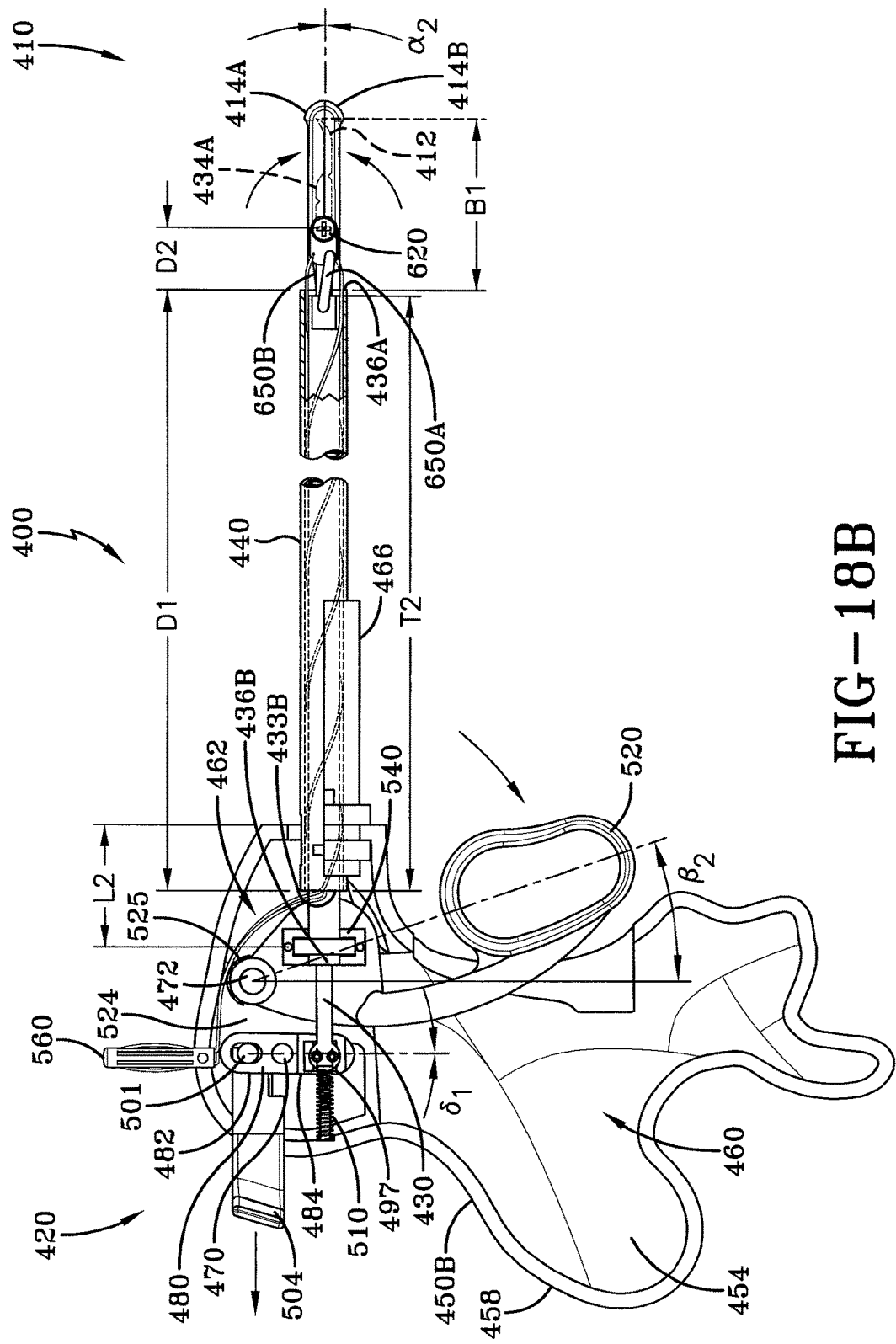
Figure 18C:
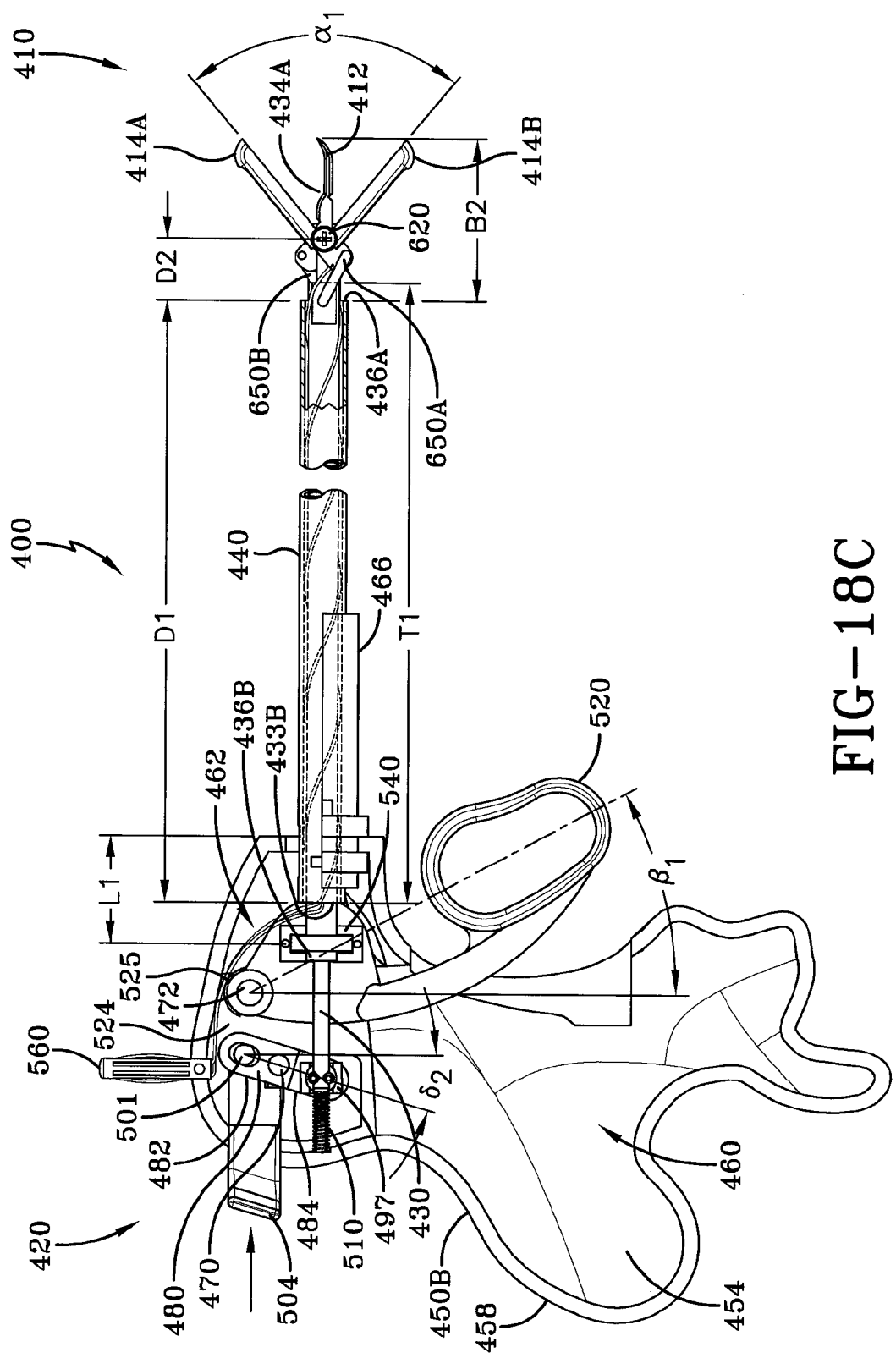
Figure 18D:
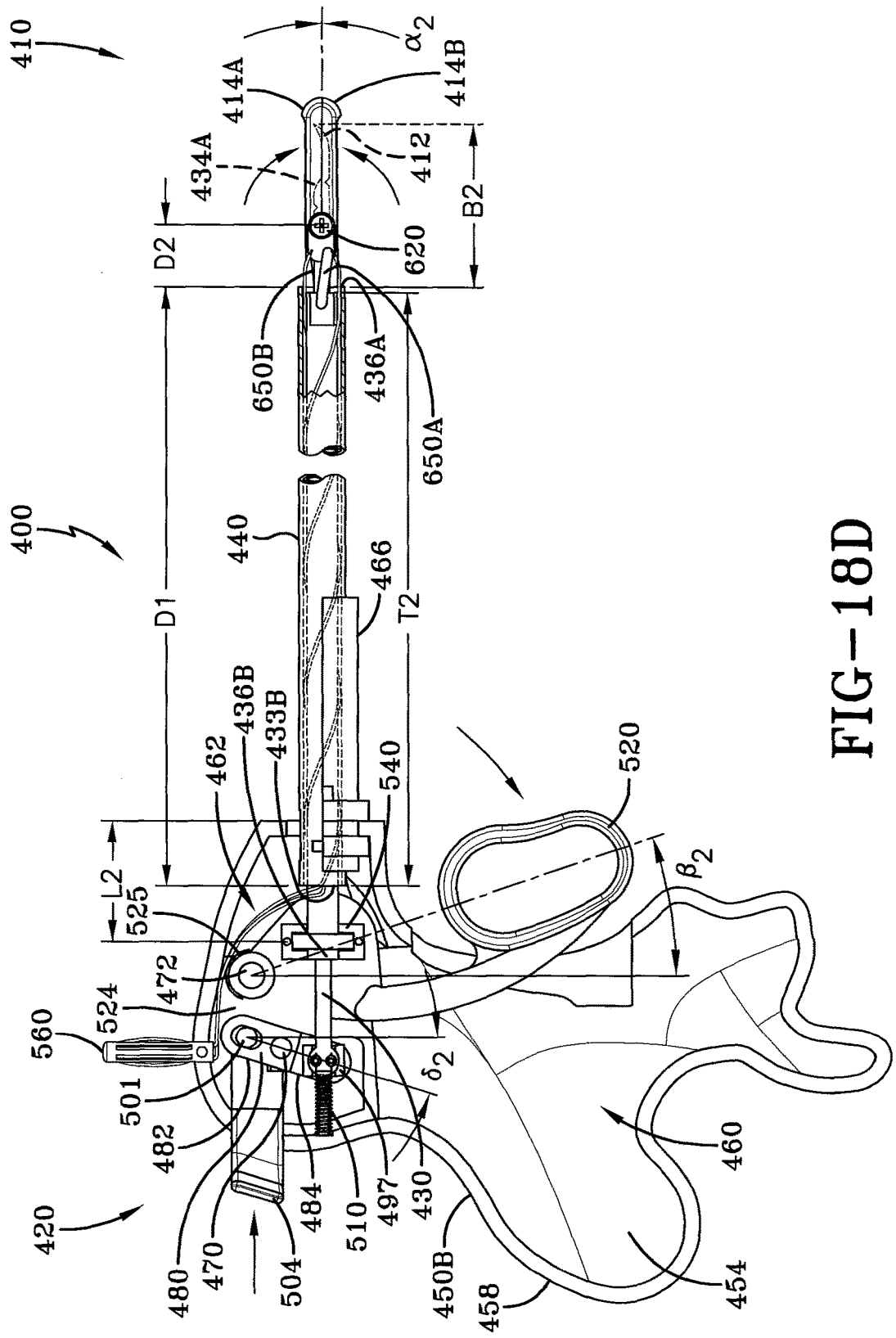
Figure 20A:
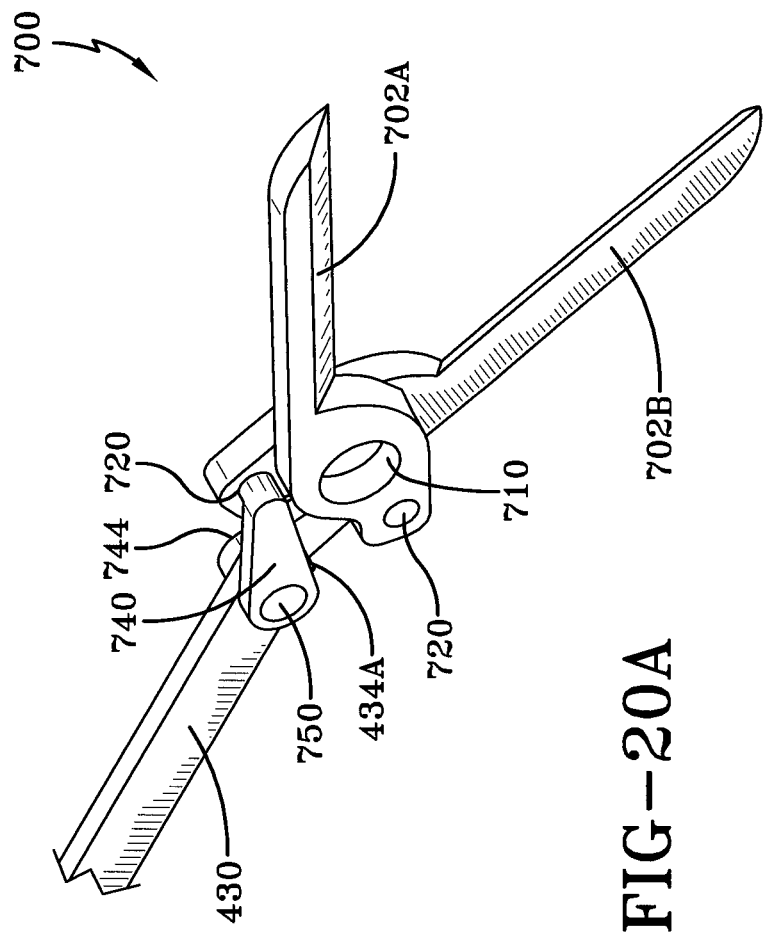
FIG. 20A is a perspective view of a scissor assembly provided by the end effector of the alternative laparoscope configured for use with the variable-frequency stimulator in accordance with the concepts of the present invention.

Thus, when the laparoscope 400 is initially placed into use whereby neither the thumb trigger 504 nor the hand trigger 520 are actuated by the user, the cutting blade 412 is extended to is normal resting position, and the grasping arms 414A-B are maintained in an opened state, as shown in FIG. 18A. When the hand trigger 520 is squeezed and the thumb trigger 504 is left in its normal resting position, the grasping arms 414A-B are closed, and the cutting blade remains in its normal resting position, as shown in FIG. 18B. Alternatively, when the thumb trigger 504 is depressed and the hand trigger 520 is left in its normal position, as shown in FIG. 18C, the cutting blade 412 is partially or fully retracted. Finally, when both the thumb trigger 504 is depressed and the hand trigger 520 is squeezed, the cutting blade 412 is fully/partially retracted, and the grasping arms 414A-B are closed, as shown in FIG. 18D.

In another aspect of the present invention, an alternative laparoscope 400' may comprise a scissor assembly 700, as shown in FIGS. 19-24, which replaces the cutting blade 412 previously discussed, with regard to laparoscope 400 shown in FIGS. 12-18. That is, the end effector 410 of laparoscope 400' is structurally equivalent to that of laparoscope 400 except that the cutting blade 412 of laparoscope 400 has been replaced with the scissor assembly 700. Specifically, the scissor assembly 700 includes a pair of scissor members 702A-B, each having a pivot aperture 710 and an actuation aperture 720, as shown in FIGS. 20A-B. A shaft 722 is disposed between attachment arms 600,602 and is received through the pivot apertures 710 of each scissor member 702A-B. In addition, linkage members 740 and 744 formed of dielectric material are pivotably attached to the actuation aperture 720 of each respective scissor member 702A-B at one end, and to pivot apertures 750 disposed on each side of the actuation member 430 at another end of the linkage members 740. In another aspect, the scissor members 702A and 702B may be separated by a dielectric or non-conductive washer (not shown), such that the scissor members 702A-B are electrically isolated from one another, so as to ensure that the grasping arms 414A-B remain electrically isolated from each other.

Figure 21A:
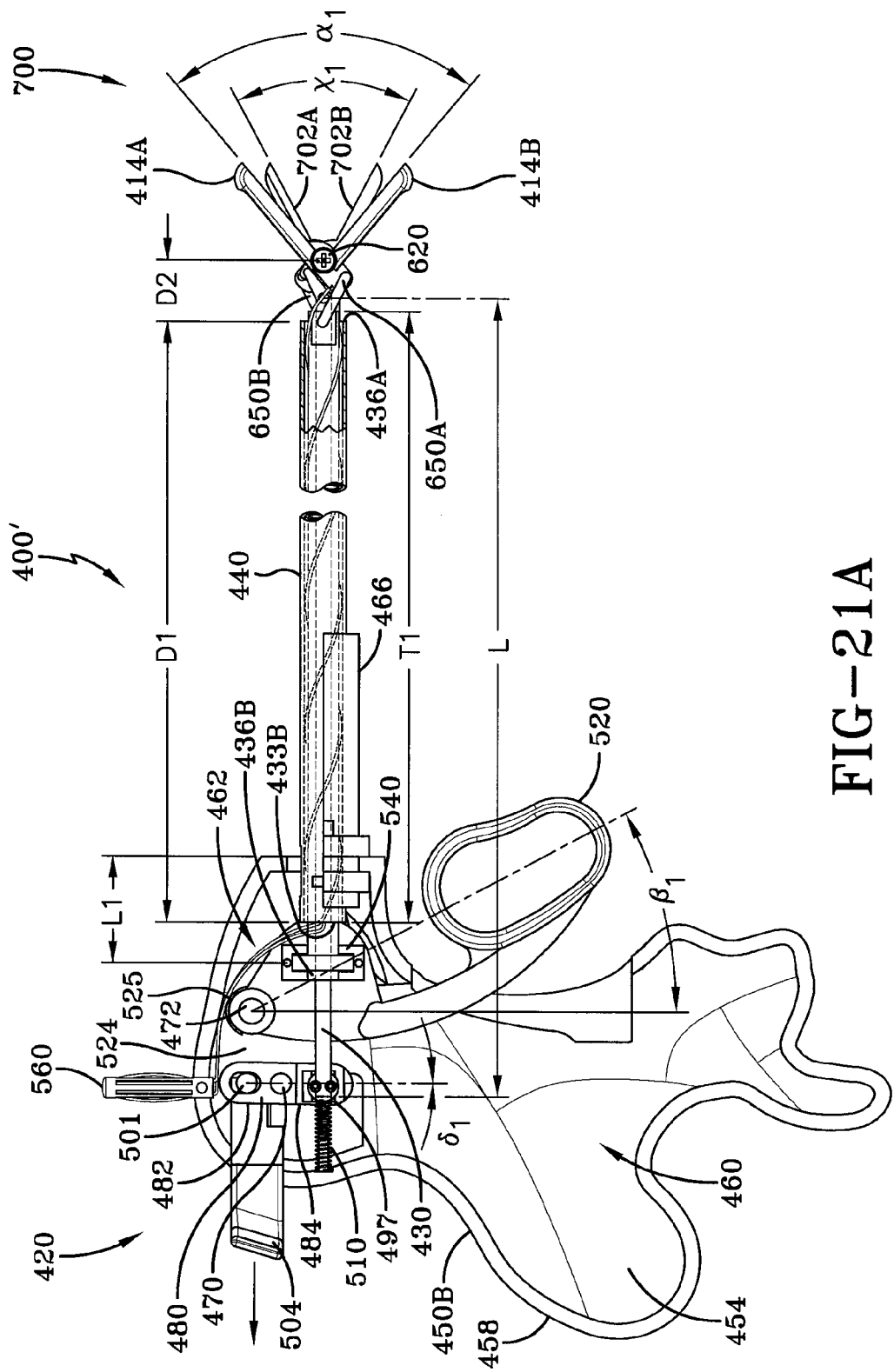
FIG. 21A is an elevational view of the grasping arms and scissor members of the alternative laparoscope configured for use with the variable-frequency stimulator in an opened position in accordance with the concepts of the present invention.
Figure 21B:
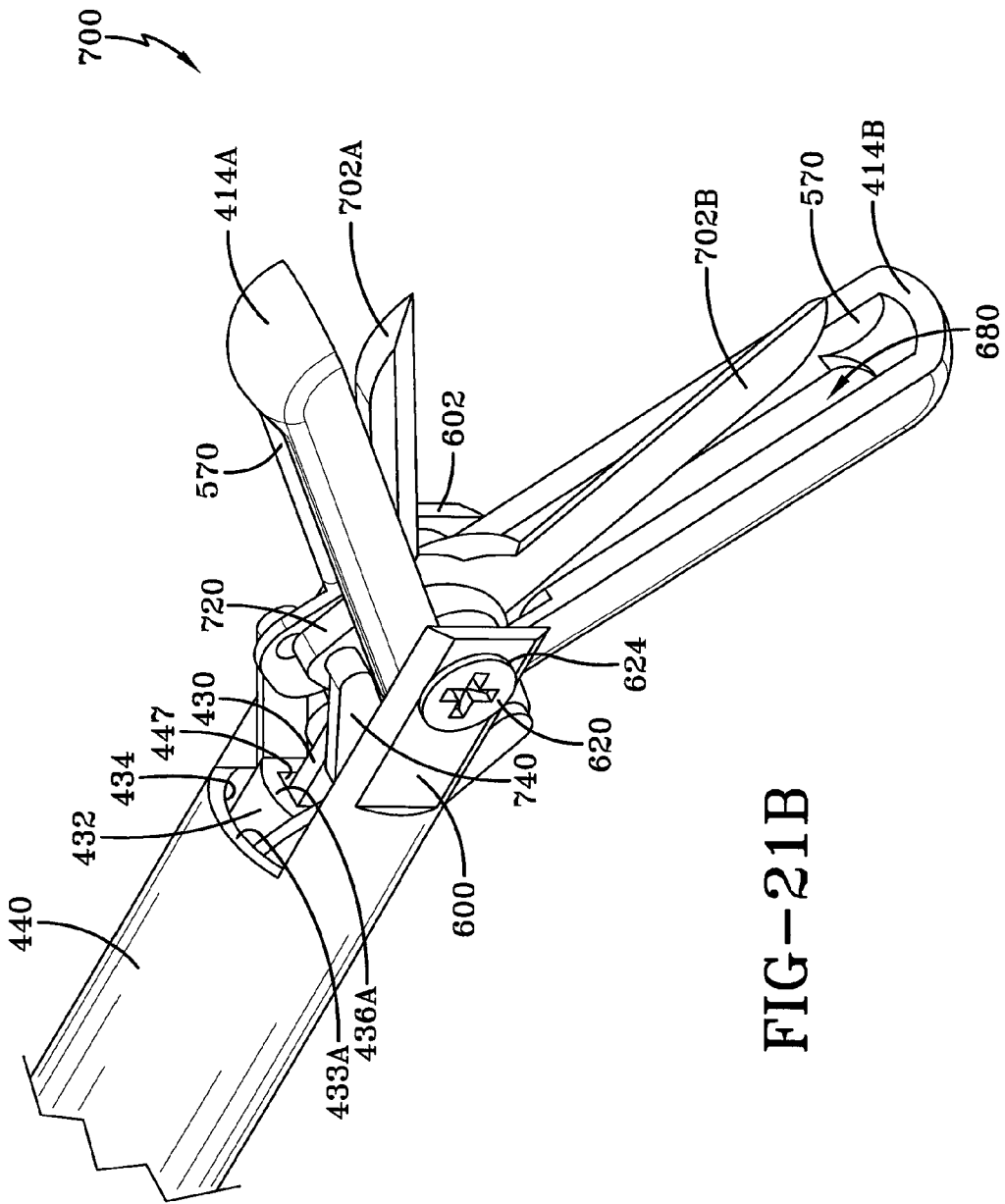
FIG. 21B is a perspective view of the grasping arms and scissor members of the alternative laparoscope configured for use with the variable-frequency stimulator in an opened position in accordance with the concepts of the present invention.
Figure 22A:
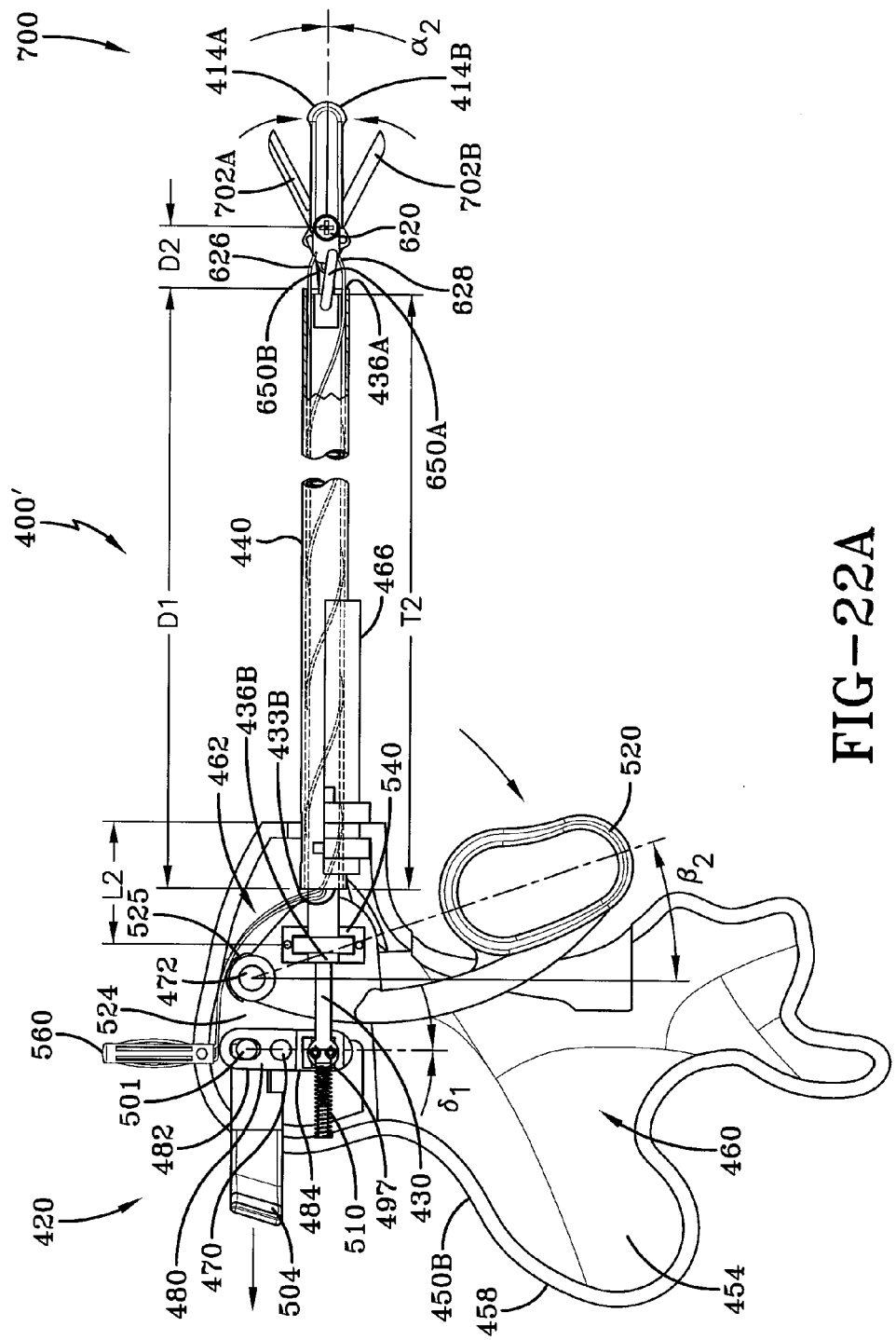
FIG. 22A is an elevational view of the alternative laparoscope configured for use with the variable-frequency stimulator, where the grasping arms are in a closed position and the scissor members are in an opened position in accordance with the concepts of the present invention.
Figure 22B:
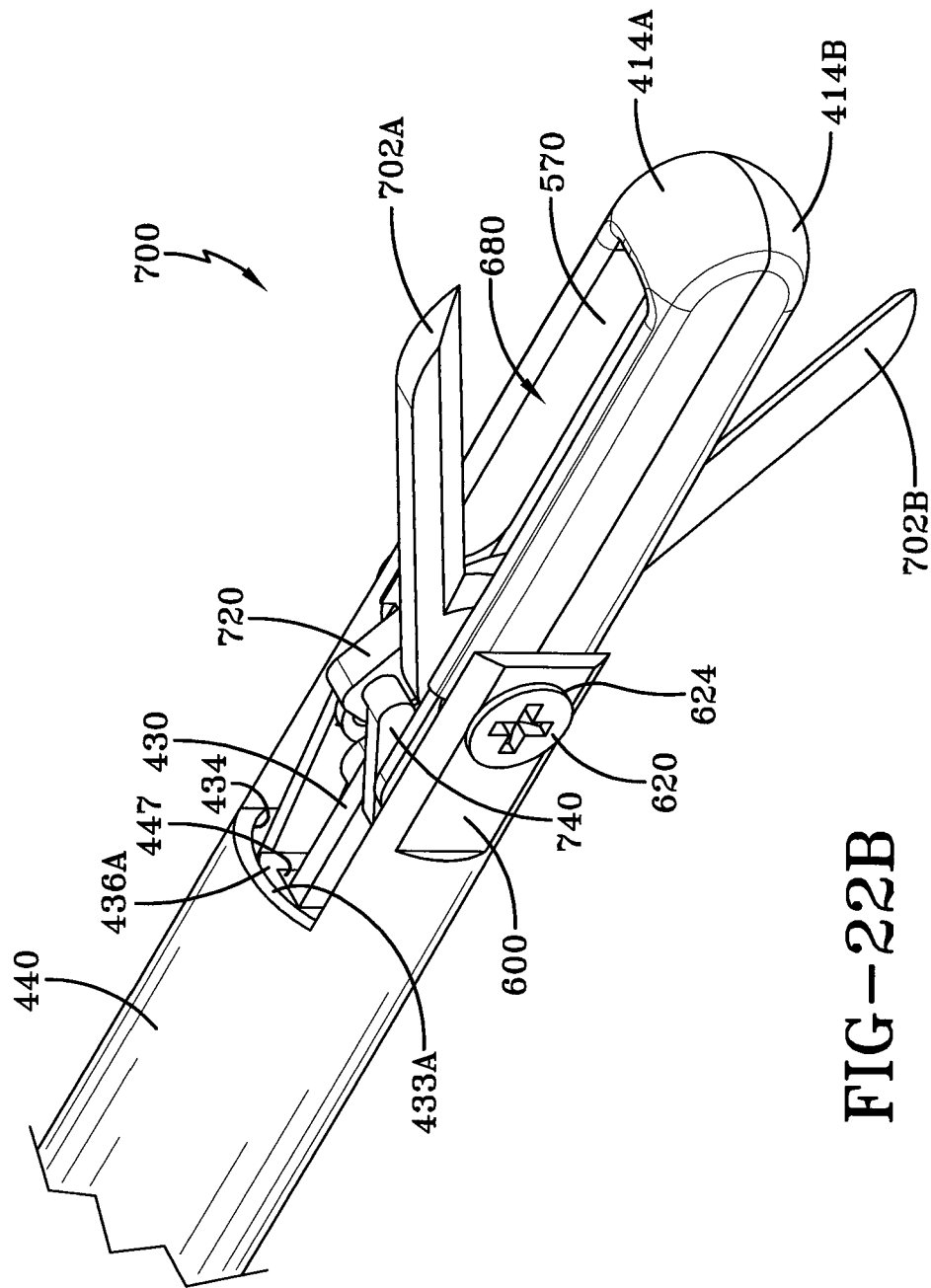
FIG. 22B is a perspective view of the alternative laparoscope configured for use with the variable-frequency stimulator, whereby the grasping arms are in a closed position and the scissor members are in an opened position in accordance with the concepts of the present invention.
Figure 23A:
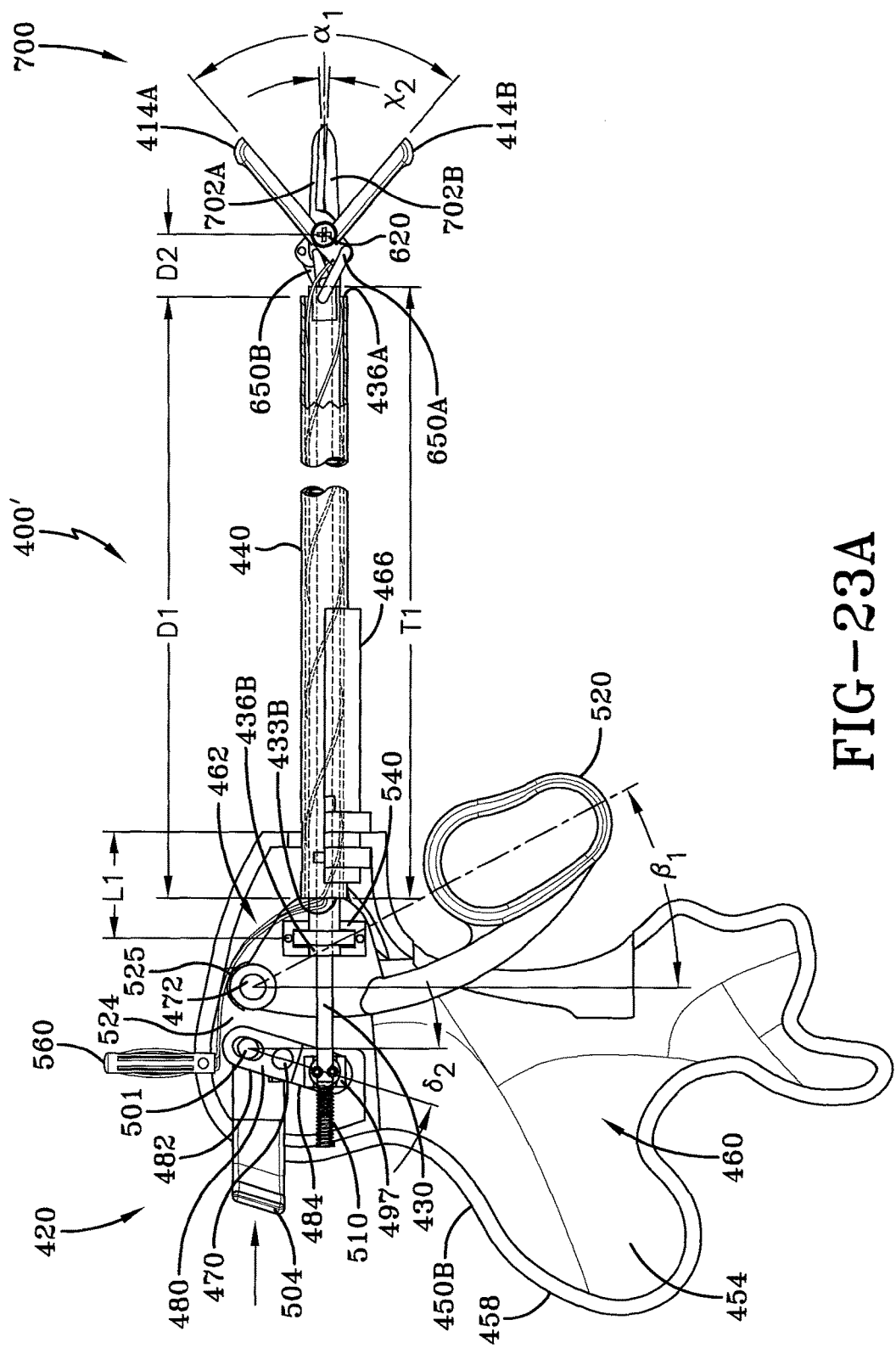
FIG. 23A is an elevational view of the alternative laparoscope configured for use with the variable-frequency stimulator, whereby the grasping arms are in an opened position and the scissor members are in a closed position in accordance with the concepts of the present invention.
Figure 23B:
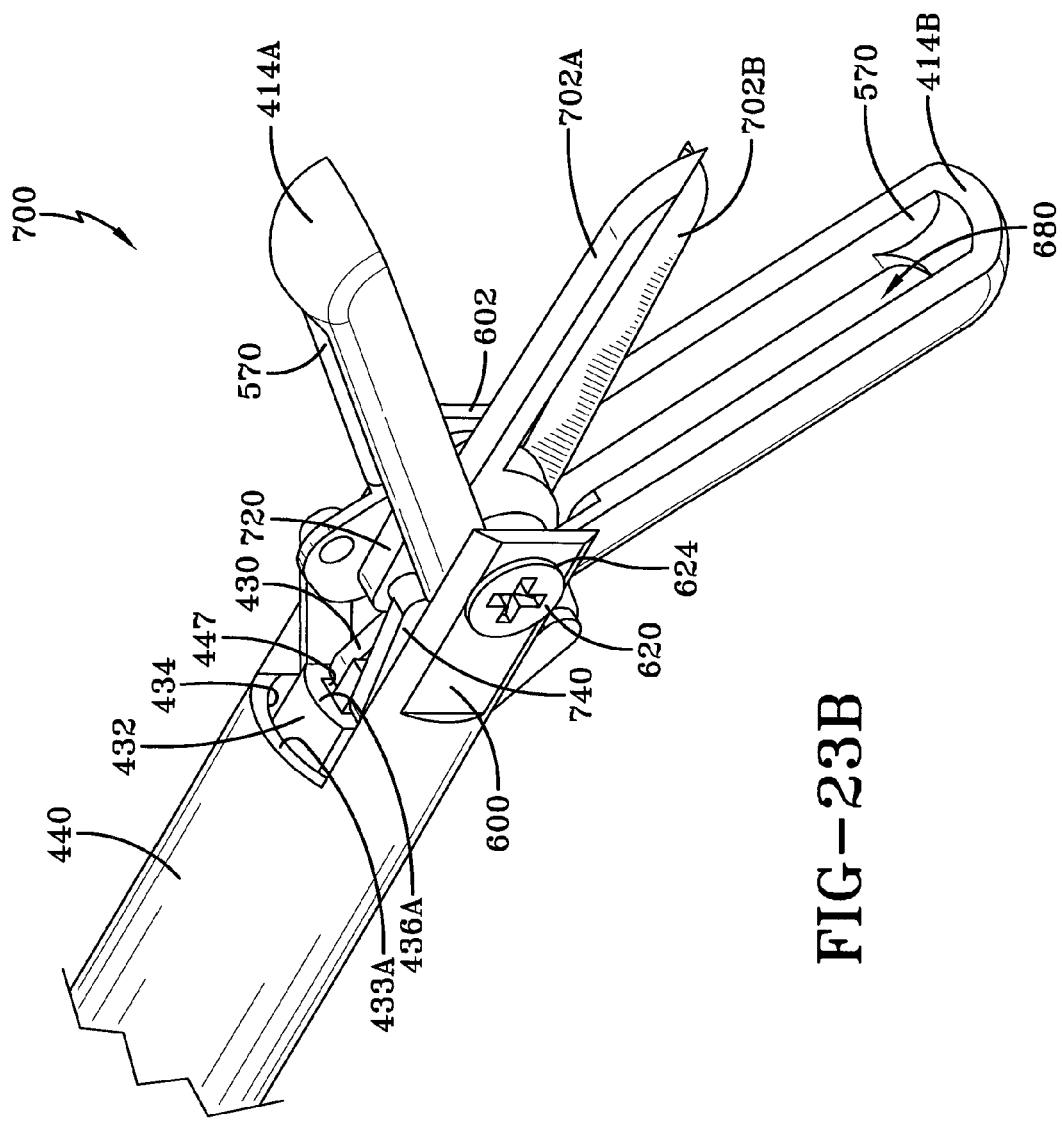
FIG. 23B is a perspective view of the alternative laparoscope configured for use with the variable-frequency stimulator, whereby the grasping arms are in an opened position and the scissor members are in a closed position in accordance with the concepts of the present invention.
Figure 24A:
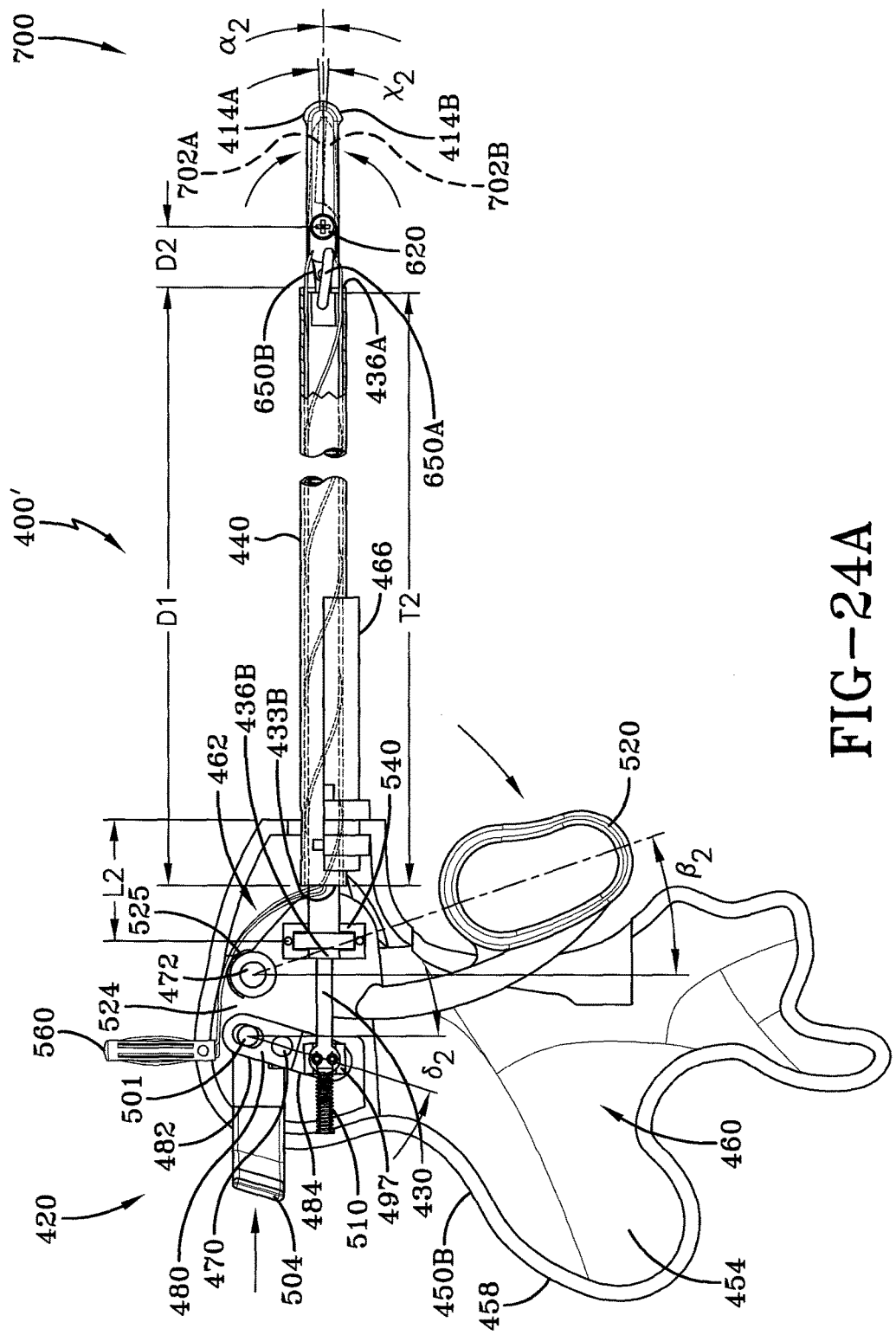
FIG. 24A is an elevational view of the alternative laparoscope configured for use with the variable-frequency stimulator, whereby the grasping arms and scissor members are in a closed position in accordance with the concepts of the present invention.
Figure 24B:
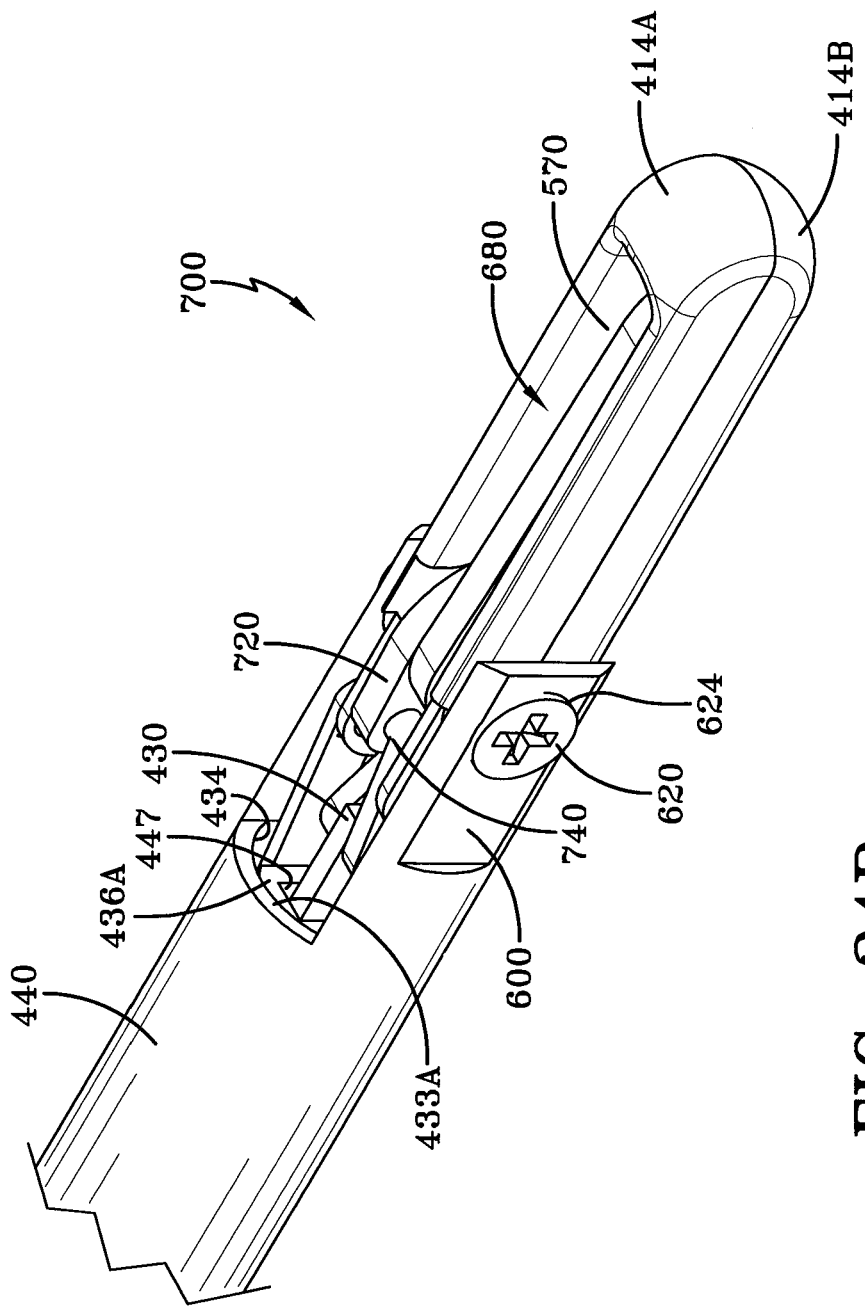
FIG. 24B is a perspective view of the alternative laparoscope configured for use with the variable-frequency stimulator, whereby the grasping arms and scissor members are in a closed position in accordance with the concepts of the present invention.
Figure 25:
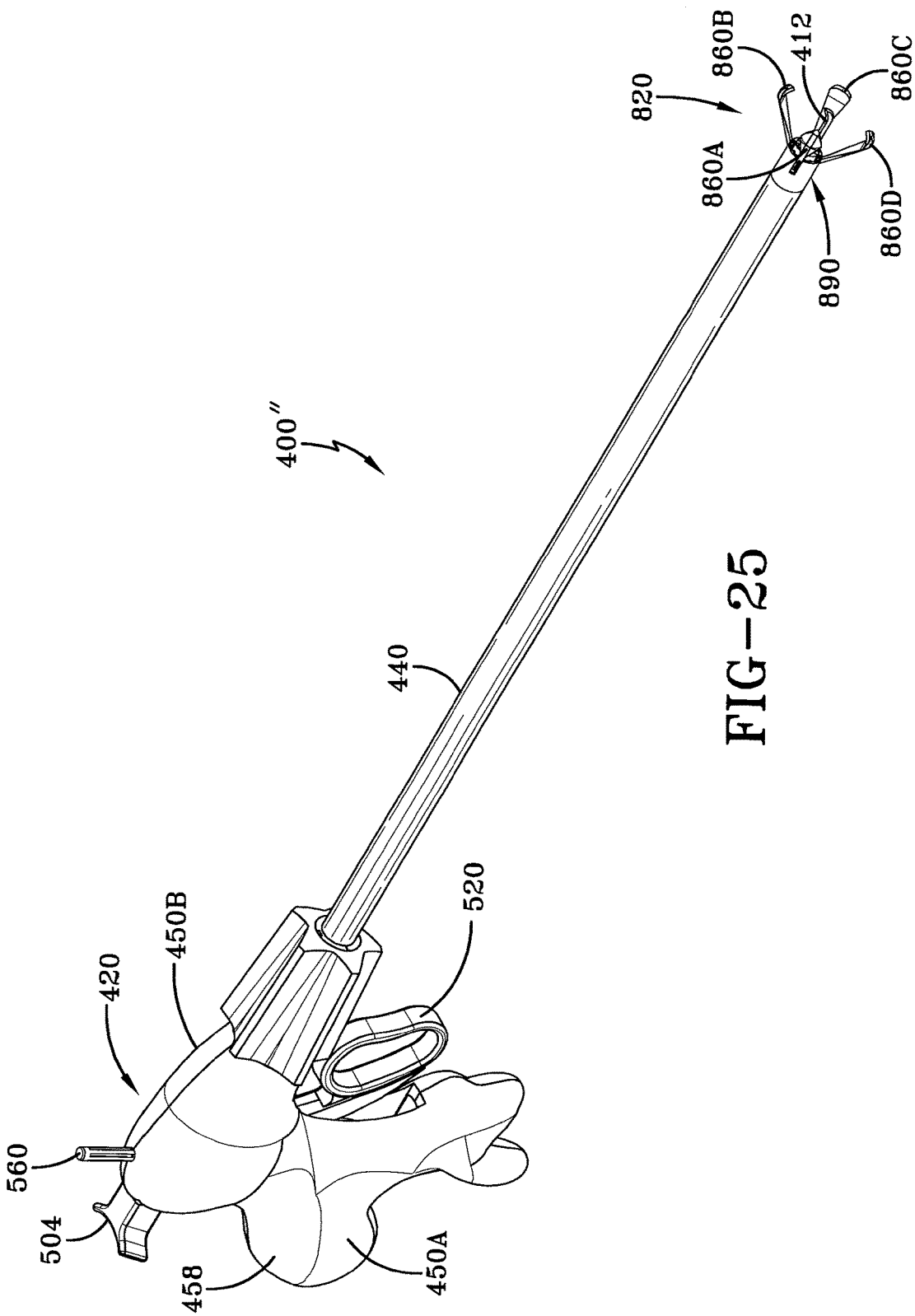
FIG. 25 is a perspective view of another alternative laparoscope having an alternative end effector configured for use with the variable-frequency stimulator in accordance with the concepts of the present invention.

Thus, during operation of the laparoscope 400', when it is in its normal resting position and the thumb trigger 504 and hand trigger 520 are not actuated, the grasping arms 414A-B and scissor members 702A-B are opened, as shown in FIGS. 21A-B. When the hand trigger 520 is squeezed and the thumb trigger 504 is not depressed, the grasping arms 414A-B are closed, as shown in FIGS. 22A-B, and the scissor members 702A-B remain opened and extend through the elongated apertures 570 of the grasping arms 414A-B. Alternatively, when the thumb trigger 504 is depressed and the hand trigger 520 is not squeezed, the scissor members 702A-B are closed, while the grasping arms 414A-B are opened, as shown in FIGS. 23A-B. Finally, when the thumb trigger 504 is depressed and the hand trigger 520 is squeezed, the scissor members 702A-B and the grasping arms 414A-B are both closed, as shown in FIGS. 24A-B.

Figure 26:
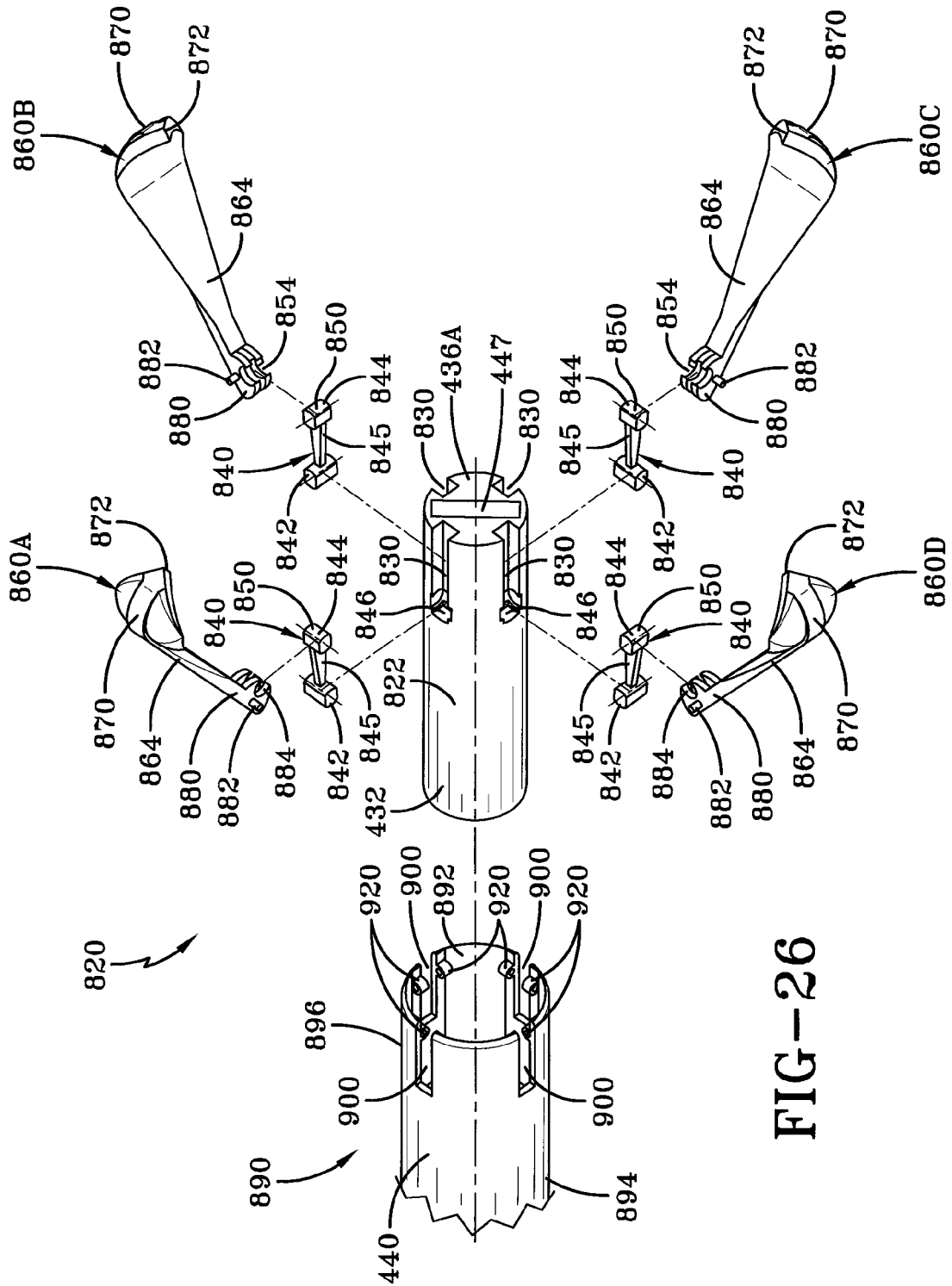
FIG. 26 is an exploded view of the grasping arms provided by the alternative laparoscope configured for use with the variable-frequency stimulator in accordance with the concepts of the present invention.

In another embodiment of the present invention a laparoscope 400", which is structurally equivalent to laparoscope 400, except that end effector 410 has been replaced with alternative end effector 820 is shown in FIGS. 25-32 of the drawings. Specifically, the end effector 820 is configured such that a plurality of spaced notches 830 are disposed about an outer surface 822 of the actuation member 432, proximate to the end 436A, as shown in FIG. 26. The notches 830 are dimensioned to receive and retain corresponding pivot tabs 840 therein, which include a fastener end 842 that is attached to an opposed pivot end 844 by an extension member 845. As such, the fastener end 842 of the pivot tab 840 is configured to be snap-fit or frictionally-fit into corresponding pivot holders 846 disposed in the notches 830 of the actuation member 432, although any other suitable pivoting means of fixation or attachment may be used. The pivot end 844 of each pivot tab 840 includes a substantially cylindrical pivot surface 850 that is dimensioned to be pivotably attached within an arcuate pivot retainer 854 provided by each grasping arm 860A-D. The grasping arms 860A-D each include a support arm 864 that extends from the arcuate pivot retainer 854, and which terminates at a curved claw 870. In one aspect, the curved claw 870 of each of the grasping arms 860A-D may terminate at a point or tip 872. Finally, extending at a substantially right angle from either side of an outer surface 880 of the grasping arm 860A-D at a point proximate to the pivot retainer 854 are pivot pins 882.

Figure 27:
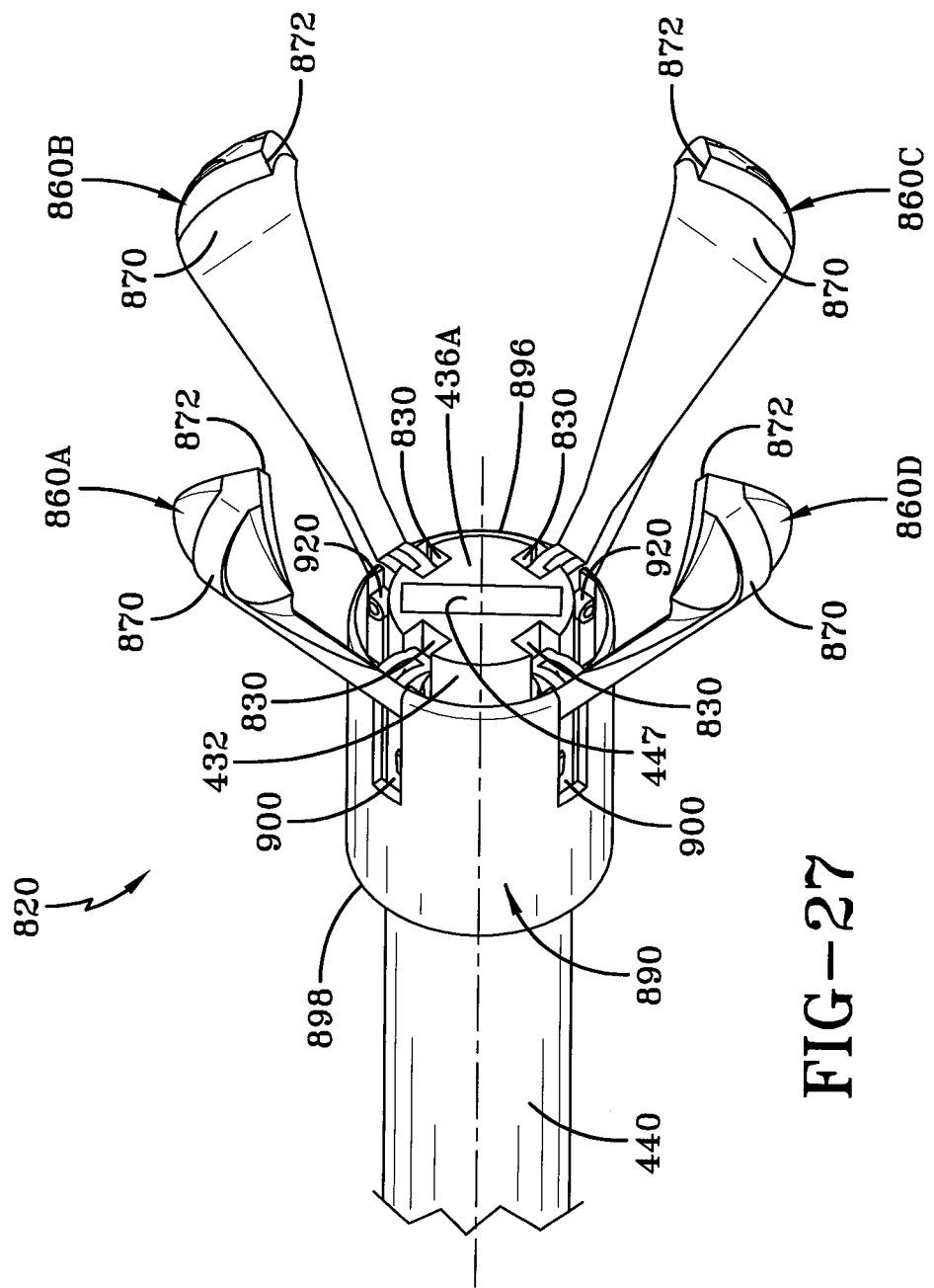
FIG. 27 is a perspective view of the alternative laparoscope configured for use with the variable-frequency stimulator showing the grasping arms in an opened position in accordance with the concepts of the present invention.

The end effector 820 of the laparoscope 400" also includes a substantially cylindrical collar member 890, as shown in FIG. 27, having an inner surface 892 and an outer surface 894, and that is terminated at opposed ends 896 and 898. The collar 890 includes a plurality of spaced notches 900 that are disposed proximate to the end 896 of the collar 890, which are dimensioned to allow the support arm 864 of the respective grasping arms 860A-D to slide therethrough. Furthermore, the collar 890 is dimensioned to receive the actuation member 432 therein, such that the notches 900 of the collar 890 are substantially aligned with the notches 830 of the actuation member 432, thereby aligning the grasping arms 860A-D to freely move through the collar notch 900. In addition, the collar 890 also includes retention apertures 920 that are disposed on either side of the notch 900 that are dimensioned to receive the pivot pins 882 of each corresponding grasping arm 860A-D therein.

Disposed within aperture 447 of the actuation member 432 is the actuation member 430 to which the cutting blade 412 is attached, as previously discussed with regard to the embodiment in FIGS. 12-18.

Figure 28:
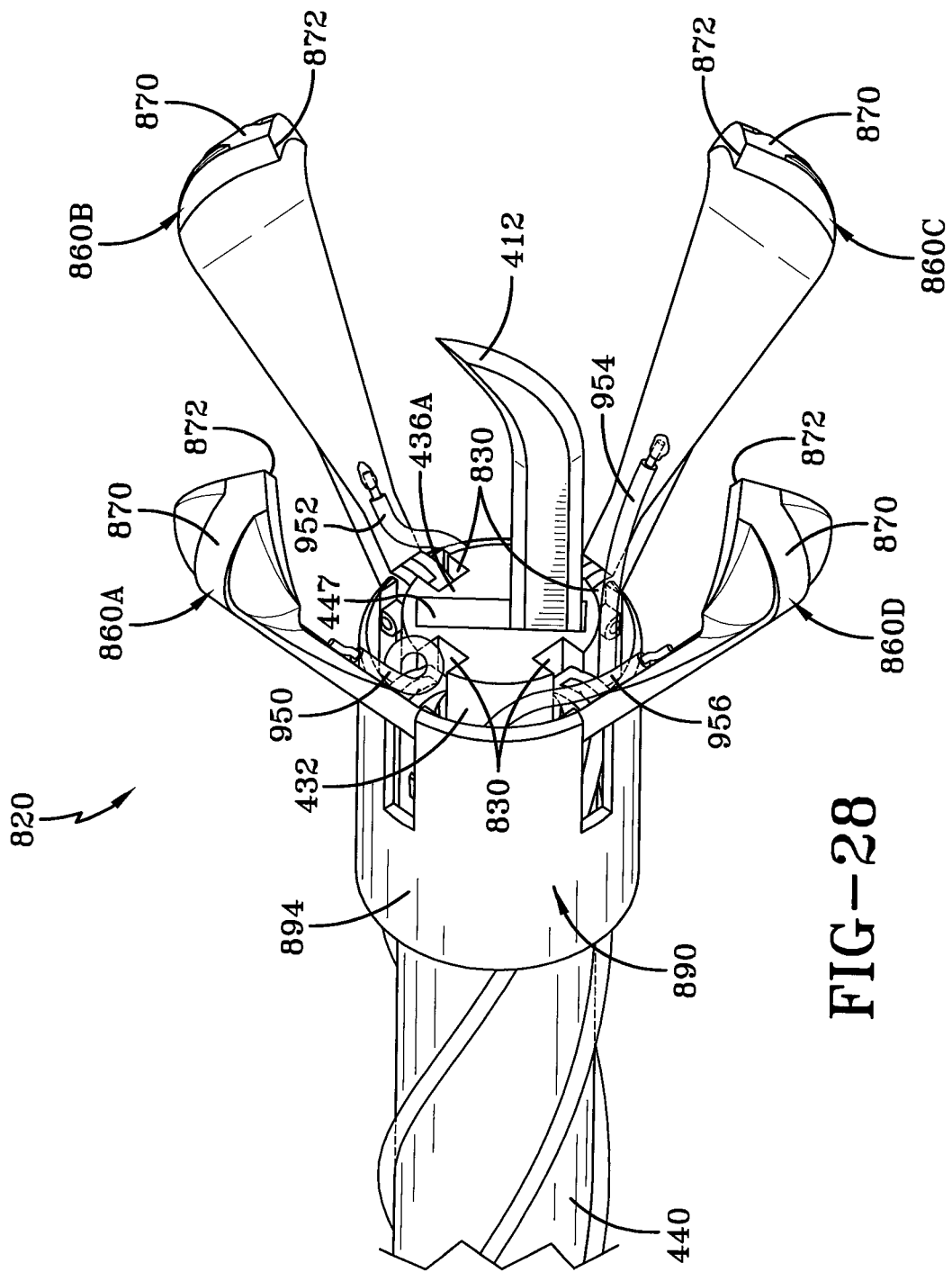
FIG. 28 is a perspective view of the alternative laparoscope configured for use with the variable-frequency stimulator showing the grasping arms in an opened position in accordance with the concepts of the present invention.

In addition, because the laparoscope 400" includes four grasping arms 860A-D, four connection wires 950, 952, 954, 956, as shown in FIG. 28, are used to connect each respective grasping arm 860A-D to the connection interface 560, such that suitable electric signals, as previously discussed, can be delivered to the grasping arms 860A-D. Furthermore, it should be appreciated that collar 890 and actuation member 432 are electrically isolated from the grasping arms 860A-D using known means, such that the grasping arms 860A-D are each electrically isolated from each other. Furthermore, in one aspect, the grasping arms 860A-D may be configured, such that arms 860A and 860C comprise positive terminals or electrodes and arms 860B and 860D comprise negative terminals or electrodes, however, it should be appreciated that the grasping arms 860A-D may be configured to be positive or negative in any desired configuration. As such, electrical signal supplied by the frequency generator 120 of the variable-frequency stimulator 100 is able to flow in multiple paths between the various positive and negative terminals or electrodes of formed by the grasping arms 860A-D, which serves to concentrate the flow of electrical current through tissue being grasped by the grasping arms 860A-D. Moreover, by concentrating the flow electrical current, collateral damage, such as overheating, charring, and burning is minimized or prevented. Furthermore, more precise tissue dissection is also enabled with more concentrated current flow.

Figure 29:
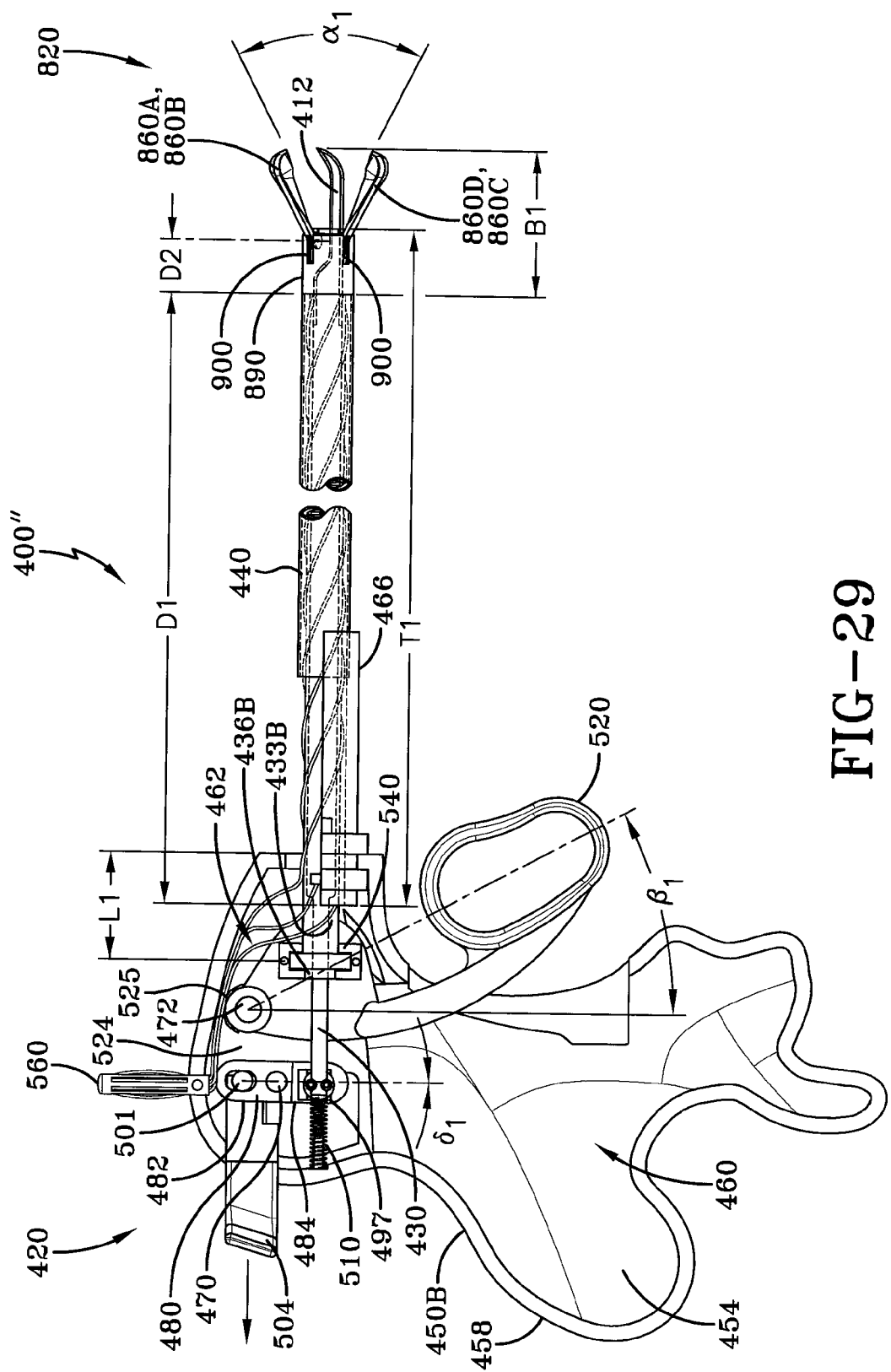
FIG. 29 is an elevational view of the alternative laparoscope configured for use with the variable-frequency stimulator showing the grasping arms in an opened position in accordance with the concepts of the present invention.
Figure 30:
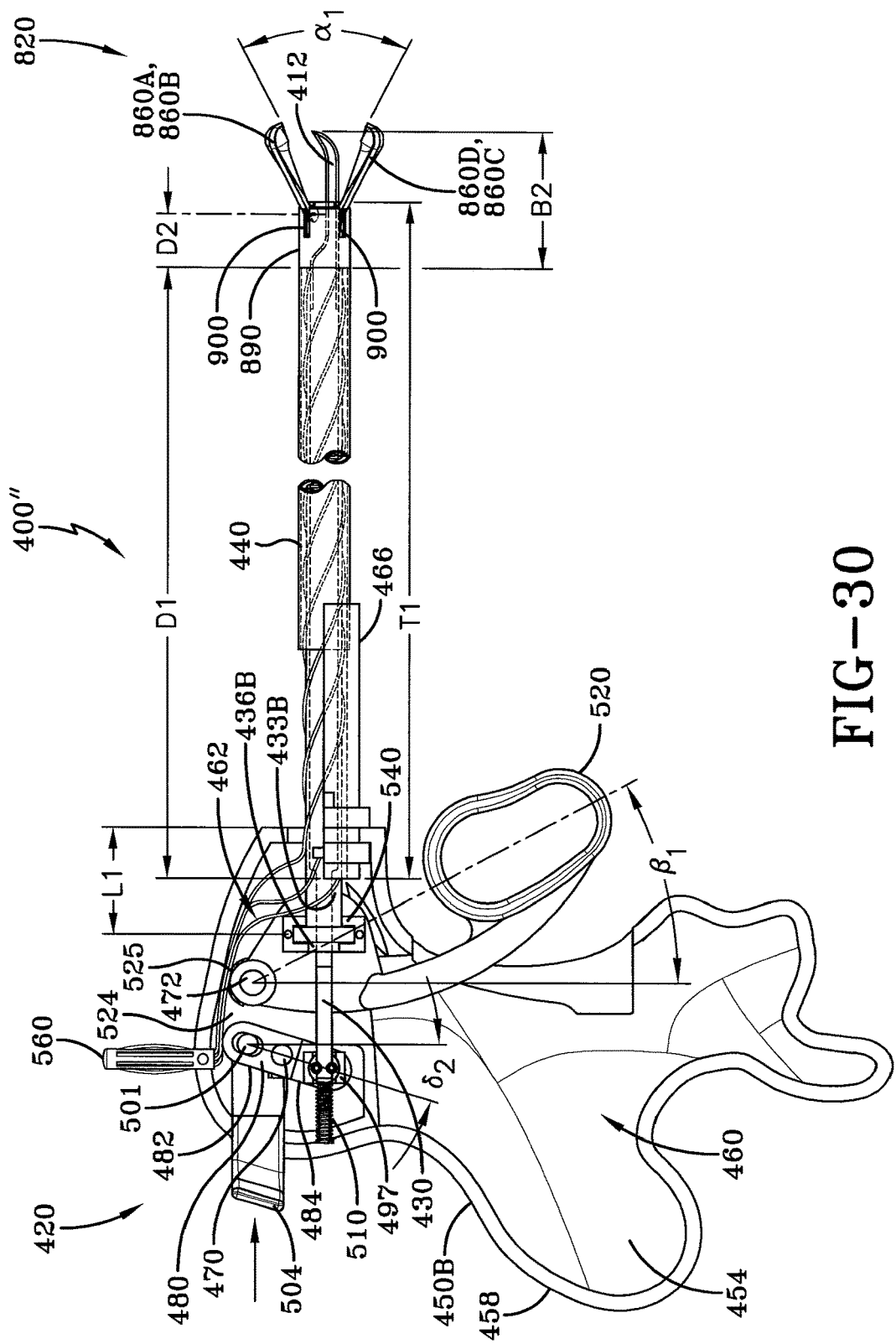
FIG. 30 is an elevational view of the alternative laparoscope configured for use with the variable-frequency stimulator showing the grasping arms in an opened position in accordance with the concepts of the present invention.
Figure 31A:
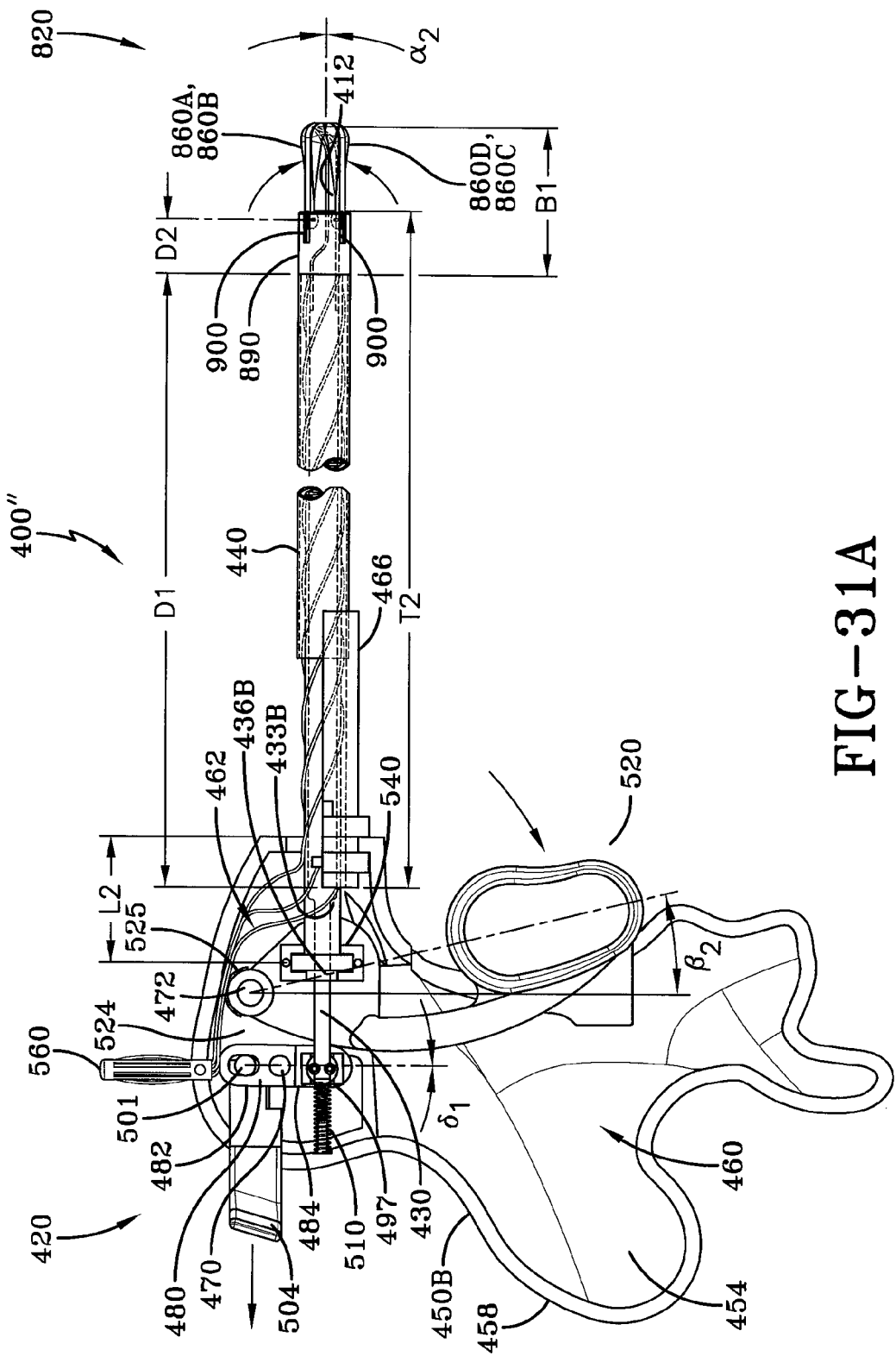
FIG. 31A is an elevational view of the alternative laparoscope configured for use with the variable-frequency stimulator showing the grasping arms in a closed position in accordance with the concepts of the present invention.
Figure 31B:
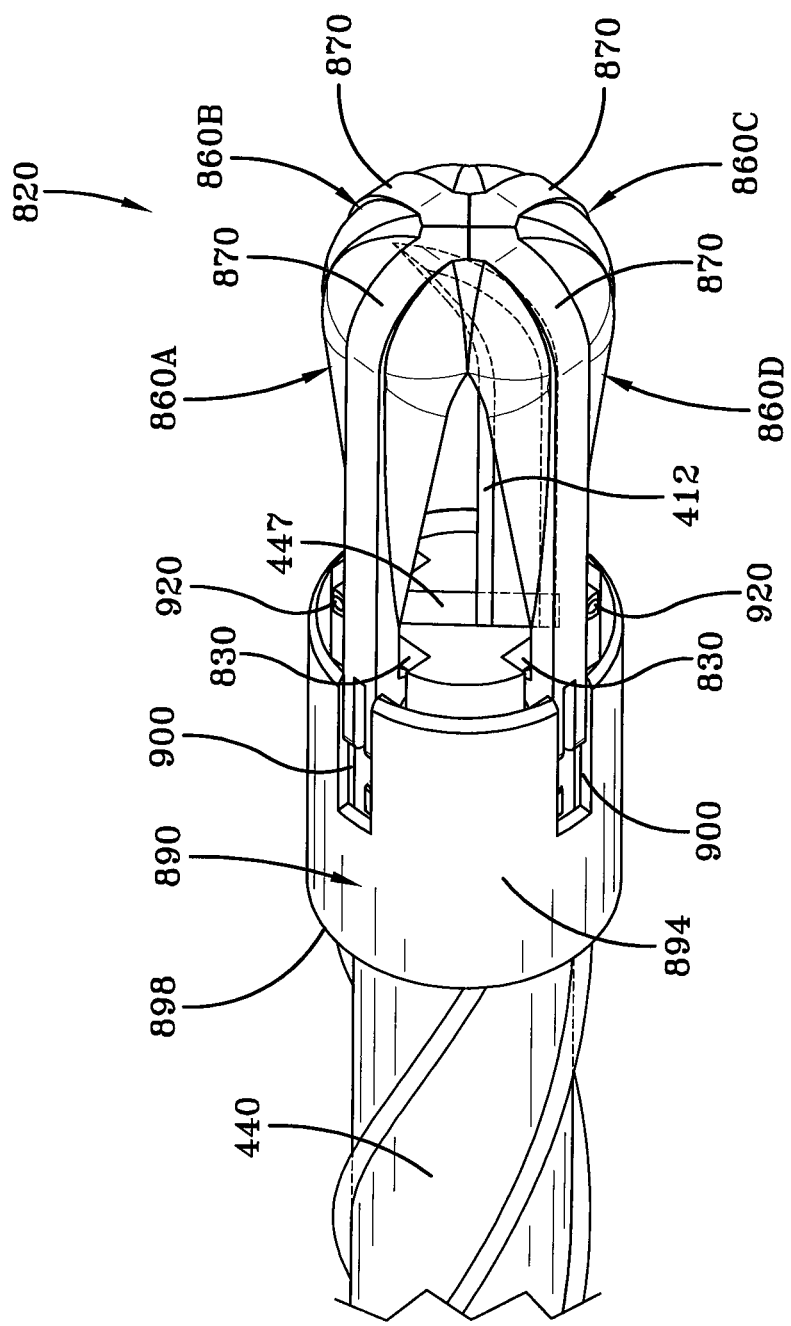
FIG. 31B is a perspective view an the alternative laparoscope configured for use with the variable-frequency stimulator showing the grasping arms in a closed position in accordance with the concepts of the present invention.
Figure 32:
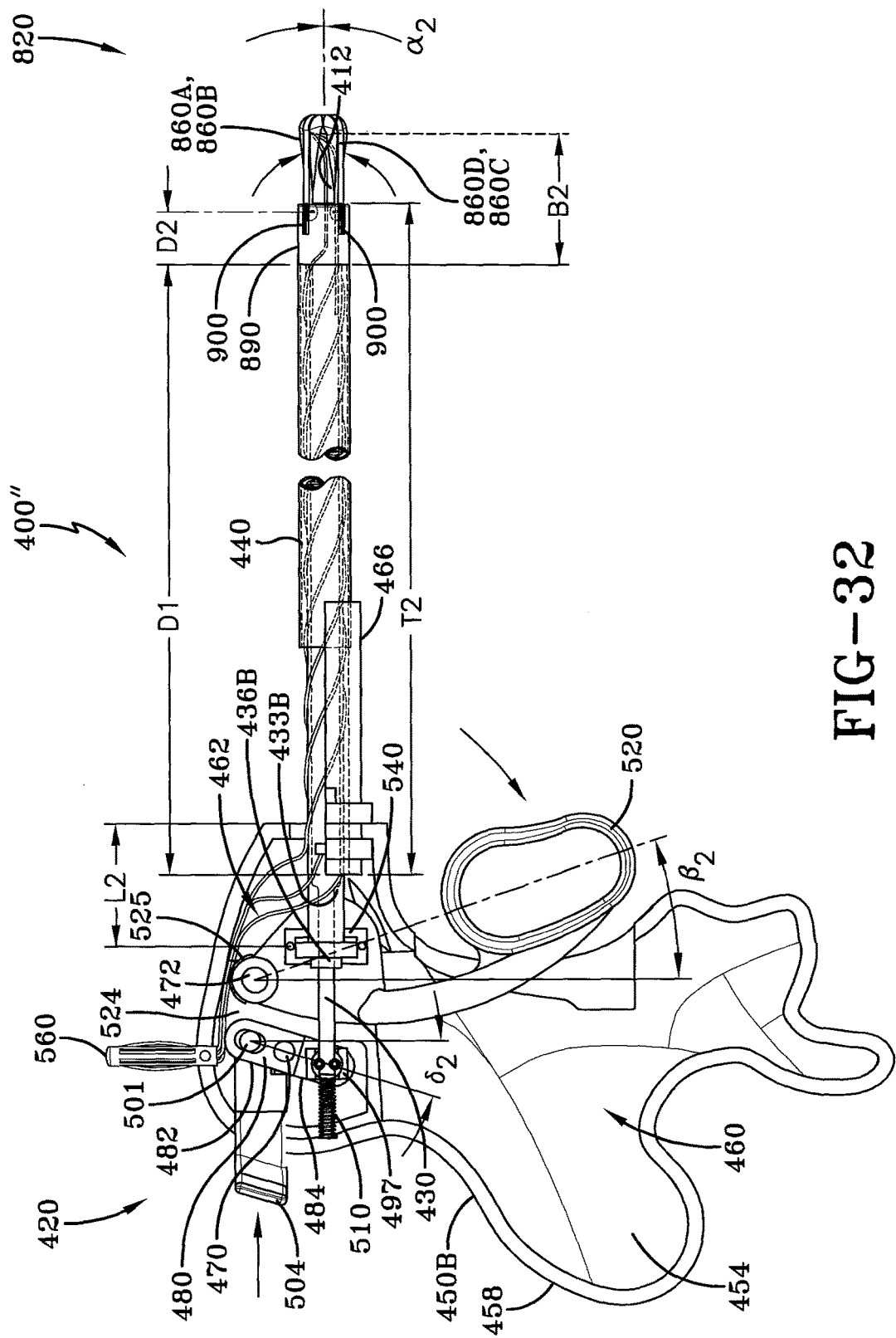
FIG. 32 is an elevational view of the alternative laparoscope configured for use with the variable-frequency stimulator showing the grasping arms in a closed position in accordance with the concepts of the present invention.

Thus, during operation of the laparoscope 400", when the laparoscope 400" is at its normal resting state, whereby the thumb trigger 504 and the hand trigger 520 are not actuated, the grasping arms 860A-D are fully opened, and the cutting blade 412 is fully extended as shown in FIG. 29. When the thumb trigger 504 is depressed, and the hand trigger 520 is not squeezed, the cutting blade 412 is partially or fully retracted into the cavity 447 of the actuation member 432, and the grasping arms 860A-D are fully opened, as shown in FIG. 30. Alternatively, when the hand trigger 520 is squeezed, and the thumb trigger 504 is not depressed, the grasping arms 560A-D are closed and the cutting blade 412 is extended, as shown in FIGS. 31A and 31B. Finally, when the thumb trigger 504 is depressed and the hand trigger 520 is squeezed, the cutting blade 412 is partially or fully retracted into the cavity 447 of the actuation member 432 and the grasping arms 860A-D are closed, as shown in FIG. 32. Thus, the reciprocating back and forth movement of the cutting blade 412 and the opening and closing of the grasping arms 860A-D can be independently controlled by the thumb trigger 504 and the hand trigger 520.

It will, therefore, be appreciated that one advantage of the present invention is that a variable-frequency stimulator for electrosurgery reduces overheating, charring, and tearing of tissue. Another advantage of the present invention is that the variable-frequency stimulator for electrosurgery utilizes a stimulation signal having a constant power. Still another advantage of the present invention is that the variable-frequency stimulator for electrosurgery allows a constant amount of power to be applied independently of the type of tissue being treated. An additional advantage of the present invention is that the variable-frequency stimulator provides a laparoscope that includes multiple grasping arms that permit electrical current to flow in multiple paths between the arms, so as to reduce the temperature of the tissue surrounding the surgical site. Yet another advantage of the present invention is that the variable-frequency stimulator for electrosurgery allows for improved electrosurgery efficacy and safety margins to be attained for not only robotic-assisted applications, such as cholestectomy, fundoplications, gastric banding, hysterectomy, prostatectomy, and colectomy, but will also enable surgeons to expand the scope of the surgical procedures that are performed and enhance advanced procedures, such as esophagectomy, gastrojejunostomy, thymectomy, thoracic parasympathectomy, lobectomy, mediastinal parathyroidectomy and left pancreatic resection, for example. Still another advantage of the present invention is that a laparoscope for use with a variable-frequency stimulator for electrosurgery allows electrical current to be distributed through the tissue being treated at multiple sites, so as to allow the electrical current to be concentrated in a more localized manner to reduce heating and excessive damage of the tissue surrounding the treatment site.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

The invention claimed is:

1. A variable-frequency stimulator for performing electrosurgery on tissue comprising:
   a controller;
   a switch coupled to said controller, said switch configured to be placed into either of a first state or a second state, and wherein said switch is adapted to be coupled to a surgical instrument;
   an impedance analyzer coupled to said switch, said impedance analyzer configured, in said first state, to identify a stimulation frequency from a range of frequencies for one or more tissue types so that the impedance of each one of said tissue types is the lowest; and
   a frequency generator coupled to said switch, said frequency generator configured, in said second state, to generate a stimulation signal having said stimulation frequency that is associated with one of said tissue types for receipt by the surgical instrument.

2. The variable-frequency stimulator of claim 1, further comprising a display coupled to said controller, which indicates the impedance and/or conductivity of the tissue being treated.

3. The variable-frequency stimulator of claim 1, wherein said surgical instrument comprises a laparoscope.

4. The variable-frequency stimulator of claim 3, wherein said laparoscope includes at least two electrically-isolated grasping arms, so as to allow the electrical signal to flow through multiple contact points in the tissue when said laparoscope is in contact therewith.

5. The variable-frequency stimulator of claim 3, wherein said laparoscope includes at least four electrically-isolated grasping arms, so as to allow the electrical signal to flow through multiple contact points in the tissue when said laparoscope is in contact therewith.

6. The variable-frequency stimulator of claim 1, wherein said controller generates an impedance ratio based on an impedance identified from one of said tissue types at a predetermined frequency, and said lowest impedance associated with said one tissue type, wherein said controller reduces an amount of power associated with said stimulation signal based on said impedance ratio.

7. A method of performing electrosurgery on tissue comprising the steps of:
   contacting a surgical device to a first tissue type;
   detecting a stimulation frequency from a range of frequencies for said first tissue type so that the impedance of said first tissue type is the lowest;
   generating for delivery to said surgical device a first stimulation signal having said stimulation frequency associated with said first tissue type;
   contacting said surgical device to a second tissue type;
   detecting a stimulation frequency from a range of frequencies for said second tissue type so that the impedance of said second tissue type is the lowest; and
   generating for delivery to said surgical device a second stimulation signal having said stimulation frequency associated with said second tissue type.

8. The method of claim 7, further comprising:
   generating an impedance ratio based on an impedance identified from said first tissue type at a predetermined frequency, and said lowest impedance associated with said first tissue type; and
   generating said stimulation signal applied to said first tissue type with a reduced amount of power based on said impedance ratio.

9. The method of claim 8, further comprising:
   generating an impedance ratio based on an impedance identified from said second tissue type at a predetermined frequency, and said lowest impedance associated with said second tissue type; and
   generating said stimulation signal applied to said second tissue type with a reduced amount of power based on said impedance ratio.

\* \* \* \* \*